(12) United States Patent
Gilman et al.

(10) Patent No.: US 6,725,447 B1
(45) Date of Patent: Apr. 20, 2004

(54) SYSTEM AND METHOD FOR GRAPHIC CREATION OF A MEDICAL LOGICAL MODULE IN THE ARDEN SYNTAX FILE FORMAT

(75) Inventors: John Gilman, Burtonsville, MD (US); Eric F. Halsey, San Diego, CA (US); Michael E. Raymer, San Diego, CA (US)

(73) Assignee: Nellcor Puritan Bennett Incorporated, Pleasanton, CA (US)

(*) Notice: Subject to any disclaimer, the term of this patent is extended or adjusted under 35 U.S.C. 154(b) by 0 days.

(21) Appl. No.: 09/551,806

(22) Filed: Apr. 18, 2000

(Under 37 CFR 1.47)

Related U.S. Application Data

(63) Continuation of application No. 09/000,191, filed as application No. PCT/US97/08949 on May 23, 1997, now abandoned.
(60) Provisional application No. 60/018,821, filed on May 31, 1996.

(51) Int. Cl.[7] .............................................. G06F 9/44
(52) U.S. Cl. ...................................... 717/105; 717/100
(58) Field of Search ................................. 717/100, 105

(56) References Cited

U.S. PATENT DOCUMENTS

| | | | | | |
|---|---|---|---|---|---|
| 4,866,635 | A | * | 9/1989 | Kahn et al. ................... 706/46 |
| 5,546,507 | A | * | 8/1996 | Staub ........................... 706/60 |
| 5,555,191 | A | * | 9/1996 | Hripcsak ..................... 709/224 |
| 5,583,758 | A | * | 12/1996 | McIlroy et al. ................. 705/2 |
| 5,608,898 | A | * | 3/1997 | Turpin et al. ................ 707/201 |
| 5,627,908 | A | * | 5/1997 | Lee et al. .................... 382/133 |
| 5,745,712 | A | * | 4/1998 | Turpin et al. ................ 345/763 |
| 5,748,850 | A | * | 5/1998 | Sakurai ......................... 706/50 |
| 5,899,985 | A | * | 5/1999 | Tanaka ......................... 706/45 |
| 5,960,419 | A | * | 9/1999 | Fagg et al. .................... 706/59 |
| 6,067,523 | A | * | 5/2000 | Bair et al. ...................... 705/3 |
| 6,108,665 | A | * | 8/2000 | Bair et al. ................. 707/104.1 |
| 6,212,677 | B1 | * | 4/2001 | Ohkubo et al. ............. 717/143 |
| 6,484,189 | B1 | * | 11/2002 | Gerlach et al. ............. 345/730 |
| 6,493,686 | B1 | * | 12/2002 | Francone et al. ............. 706/12 |
| 2003/0130973 | A1 | * | 7/2003 | Sumner et al. ............... 706/45 |

FOREIGN PATENT DOCUMENTS

WO    WO 97/20592    6/1997

OTHER PUBLICATIONS

"Arden Syntax Overview", Apr. 1992, last update Sep. 26, 2002, retrieved from http://cslxinfmtcs.edu/hl7/arden on Feb. 19, 2003.*

(List continued on next page.)

*Primary Examiner*—Wei Zhen
*Assistant Examiner*—Mary Steelman
(74) *Attorney, Agent, or Firm*—Fulwider Patton Lee & Utecht, LLP

(57) ABSTRACT

The system and method for graphic creation of a medical logical module in the Arden syntax file format allows a user to define a medical decision process in terms of flowcharts and outlines. The system and method provide for creation of a medical logical module for a computer in the Arden syntax file format. A graphic representation of a medical decision logic tree of a connected series of a plurality of nodes in a medical decision process is encoded, with each node having a logical path from the node, and each connected series of nodes containing at least one intermediate node and a concluding node. For each node, a conditional statement is encoded for each path from the node; a definition of a path for each intermediate node is encoded; and an outcome for each concluding node is encoded.

6 Claims, 25 Drawing Sheets

OTHER PUBLICATIONS

De Martino, D, Corsorti F, Assenza M., Ferri F., Gargiulo A., Lombardi A., Martinis G., Di Paola M. "SIDIM: in Information System to Increase the Efficiency and Quality of Care", 1992, IEEE, retireved from IEEE database Feb. 19, 200.*

Pelig, Mor, Oguynyemi, Omolola, et al. "Using Features of Arden Syntax with Object–Oriented Medical Data Models for Guidelin Modeling", Computer Biomed Res 1994, retrieved from 222–smi. stanford.edu/pubs/SMI_Reports/SMI–2001–0879.pdf on Feb. 19, 2003.*

Hripcsak, George and Pryor, T.A., "SCAMC Tutorial Writing Medical Rules for Computers Using the Arden Syntax for Medical Logic Modules", 1994, retrieved from google.com Feb. 19, 2003.*

XP002049667, Gao X et al., Sep. 19, 1992.

* cited by examiner

SYSTEM AND METHOD FOR GRAPHIC CREATION OF A MEDICAL LOGICAL MODULE IN THE ARDEN SYNTAX FILE FORMAT

RELATED APPLICATION

This application is a continuation of Ser. No. 09/000,191, filed Feb. 6, 1998, now abandoned, which is a 371 of PCT/U597/08949 filed May 23, 1997, which is a U.S. provision of Ser. No. 60/018,821, filed May 31, 1996.

BACKGROUND OF THE INVENTION

Attached is an Appendix on a single compact disc, provided in duplicate, containing the twelve files Chartt~1frm, Cnodecls, Editorbas, Editform, Eznetbas, Frmnew~1frm, Mdimainfrm, Protor~1frm, Protorunbas, Protorunfrm, Runtimevpb, and Saveopenfrm, which are incorporated by reference herein, containing source code for software utilized in the invention.

1. Field of the Invention

This invention relates generally to systems and methods for developing and using medical logical modules for encoding medical protocols and information, and more particularly concerns a system and method for development and use of medical logical modules in the Arden syntax file format.

2. Description of Related Art

The Arden Syntax for medical logic modules (MLMs) is a computer programming language for encoding medical knowledge. Each medical logical module typically contains logic or information allowing a user to make one or more medical decisions, and can generate output such as e-mail messages, clinical alerts, interpretations, diagnoses, screening for clinical research, quality assurance functions, and administrative support, for example. With an appropriate computer program, also known as an event monitor, a medical logic module can run automatically, to generate advice as needed. For example, a medical logic module can provide a warning and advice to health care workers when a patient develops new or worsening kidney failure. The Arden Syntax for medical logic modules has been used extensively, for example, at Columbia-Presbyterian Medical Center in New York, and other major medical institutions and universities.

One major functional component of a medical logical module is to define the context, also termed the evoke slot, in which the medical logical module will be used, such as defining when the medical logical module is pertinent, or whether the medical logical module will be used in conjunction with data storage, another medical logical module, or another application. Another major functional component of a medical logical module is the logic, or logic slot, such as a set of medical criteria or algorithm, for example, and concluding whether a logical outcome is true or false. The medical logical module can then perform some form of action function, or action slot, to be executed when the logic concludes true, such as to store a message, send e-mail, or return a value, for example. The medical logical module maps the action to a data slot, such as to an institution's local database. For example, medical logical modules can generate a coded or narrative message; a clinical message or alert sent to the provider taking care of a patient; a warning of some concern which is usually flagged in some way; an interpretation or message of advice or information, including diagnosis support; or a screen, which typically results in a message, often sent by e-mail, to a researcher or quality assurance officer informing them of a patient that fits some criteria. Medical logical modules can also trigger each other, and can perform specific actions specific to an institution, such as communicating with another programming application or data base.

Currently, in order for a user such as a medical professional to generate an Arden syntax medical logic module, the user must be proficient in the Arden syntax, and use an Arden syntax editor program to define a medical logical module which can be shared with other medical institutions in accordance with the ASTM E31.15 standard. This can be a tedious process, which limits the accessibility of the Arden syntax for creation of medical logical modules to those willing to invest the time to learn this syntax. The majority of medical logical modules have therefore commonly been created in research and university settings. It is therefore desirable to provide a system and method that would allow a user to define a medical decision process in a medical logical module in terms of flowcharts and outlines in a manner that is more intuitive than with a conventional editor. For example, a large number of respiratory care departments in hospitals have defined therapist or patient driven protocols in the form of a flowchart. It would be much more difficult for those users to document those medical decisions in an Arden syntax format. It would be desirable to provide a method and system that would allow a user to quickly define an Arden syntax file based upon current protocols with a graphic software tool. It would be desirable to provide such a system and method that utilize user defined instructions in run time format, with a graphic user interface that visualizes the user defined protocols in a flow chart format, that can provide real time clinical decision support, and that can be integrated with existing hospital information systems. The present invention meets these needs.

SUMMARY OF THE INVENTION

Briefly, and in general terms, the present invention provides for a system and method for graphic creation, development, and utilization of a medical logical module in the Arden syntax file format that allows a user to define a medical decision process in terms of flowcharts and outlines, which is much more intuitive than an editor. The graphic software tool of the invention permits a user to quickly define an Arden syntax file by simply reducing their current protocols in flowchart and outline form. The system and method of the invention provide a graphic software tool that facilitates utilization of the ASTM standard concerning medical logical modules by the clinical community. The system and method of the invention utilize user defined instructions in run time format, with a graphic user interface that visualizes the user defined protocols in a flow chart and outline format, along with real time clinical decision support. The Arden syntax editor hardware and software system and method of the invention permits graphic creation of Patient Driven Protocols (PDPs), and point of care execution of PDPs. The system provides a software module deliverable on multiple product platforms, that can be integrated with existing hospital information systems.

Accordingly, the present invention provides for a method for creation of a medical logical module for a computer in the Arden syntax file format. The method of the invention comprises encoding a graphic representation of a medical decision logic tree of a connected series of a plurality of nodes in a medical decision process, each node having a logical path from the node, and each connected series of nodes containing at least one intermediate node and a concluding node. The graphic representation is preferably in the form of either a flowchart or an outline. For each node, a conditional statement is encoded for each path from the node; a definition of a path from each intermediate node is encoded; and an outcome for each concluding node is encoded. In a presently preferred embodiment, the outcome is selected from the group consisting of a recommended alert, an order, an action to be taken with the patient, a coded message, a narrative message, a screen, triggering of another medical logical module, and communicating with another programming application. A medical logical module of the graphic representation is also encoded in Arden Syntax file format, which in one presently preferred embodiment conforms to the current ASTM standard E31.15 (Health Knowledge Representation). An existing medical logical module can be edited through the use of graphic editor, and a graphic representation can be created of an existing Arden syntax medical logical module.

The present invention also provides for a system for creation of a medical logical module for a computer in the Arden syntax file format. In one presently preferred embodiment, the system comprises means for encoding a representation of a medical decision logic tree in a form of a graphic flowchart or outline of a connected series of a plurality of nodes in a medical decision process, each node having a logical path from the node, and each connected series of nodes containing at least one intermediate node and a concluding node; means for encoding a conditional statement for each path from each node. The system includes means for encoding a definition of a path from each intermediate node, and means for encoding an outcome for each concluding node. In a presently preferred embodiment, the outcome is selected from the group consisting of a recommended alert, action or order to be taken with the patient as defined by the medical logical module designer, a coded message, a narrative message; a screen, which typically results in a message, often sent by e-mail, to a researcher or quality assurance officer informing them of a patient that fits some criteria, triggering another medical logical module, and communicating with another programming application. The system also includes means for generating a medical logical module in Arden Syntax file format, which in one currently preferred embodiment conforms to a current ASTM standard E31.15 (Health Knowledge Representation). The system also preferably comprises means for inputting an Arden syntax medical logical module to the system and for creating and editing a graphic representation of the Arden syntax medical logical module.

These and other aspects and advantages of the invention will become apparent from the following detailed description, and the accompanying drawings, which illustrate by way of example the features of the invention.

DETAILED DESCRIPTION OF THE PREFERRED EMBODIMENTS

Figure 1:
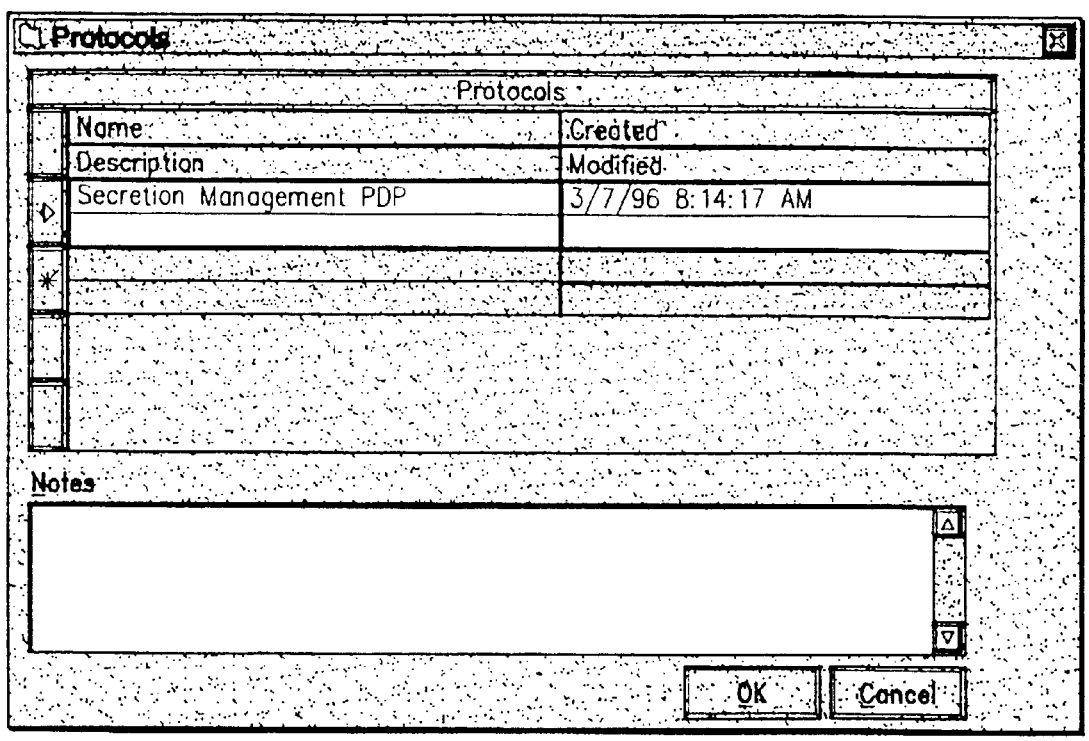
FIG. 1 is a computer screen shot of an opening screen for an example of a graphic representation of the invention of a medical logical module entitled a Secretion Management Patient Driven Protocol.
Figure 2:
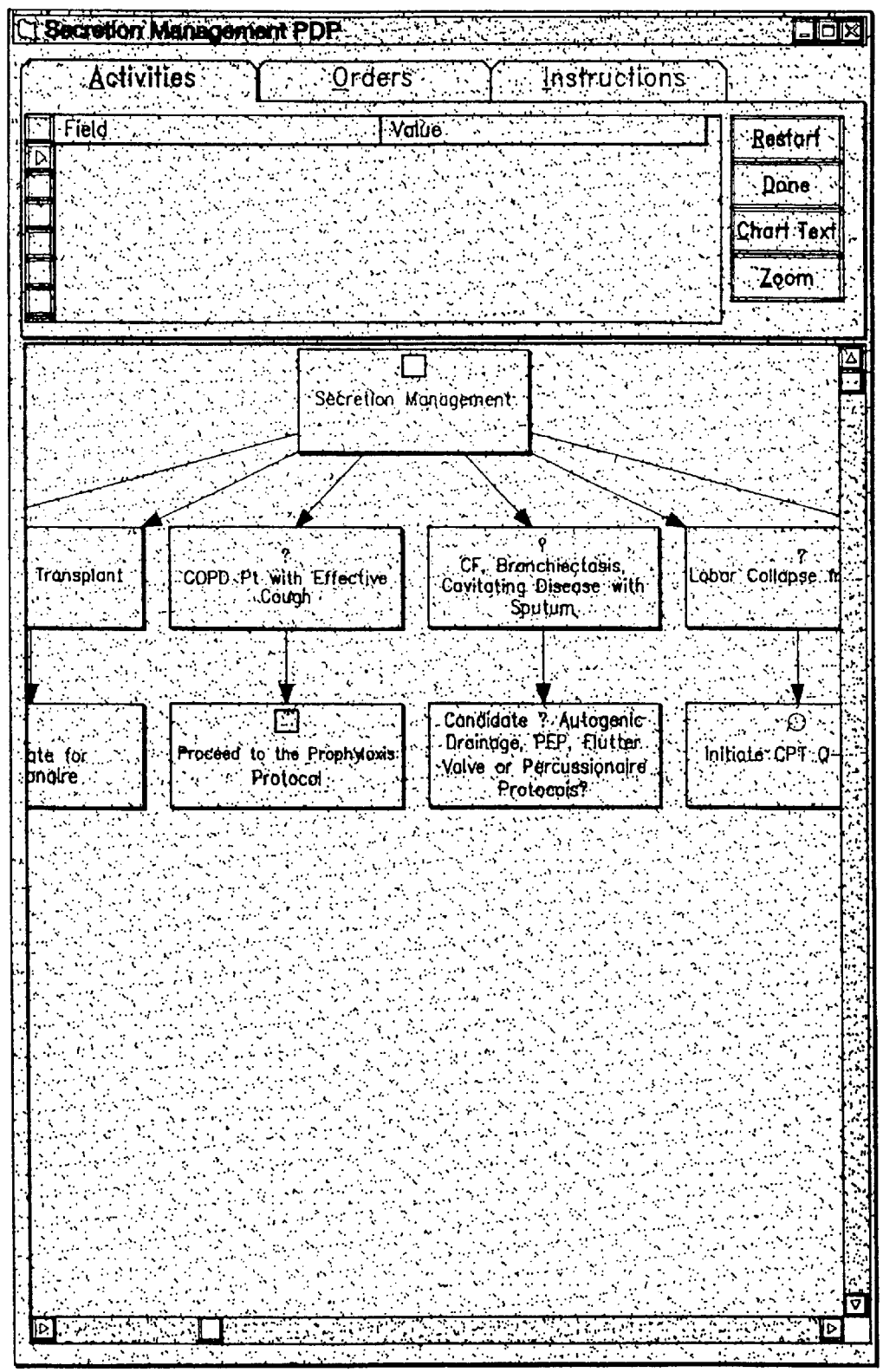
FIG. 2 is a computer screen shot of a graphic flowchart representation of the medical logical module of FIG. 1 with the Activities menu selected.
Figure 3:
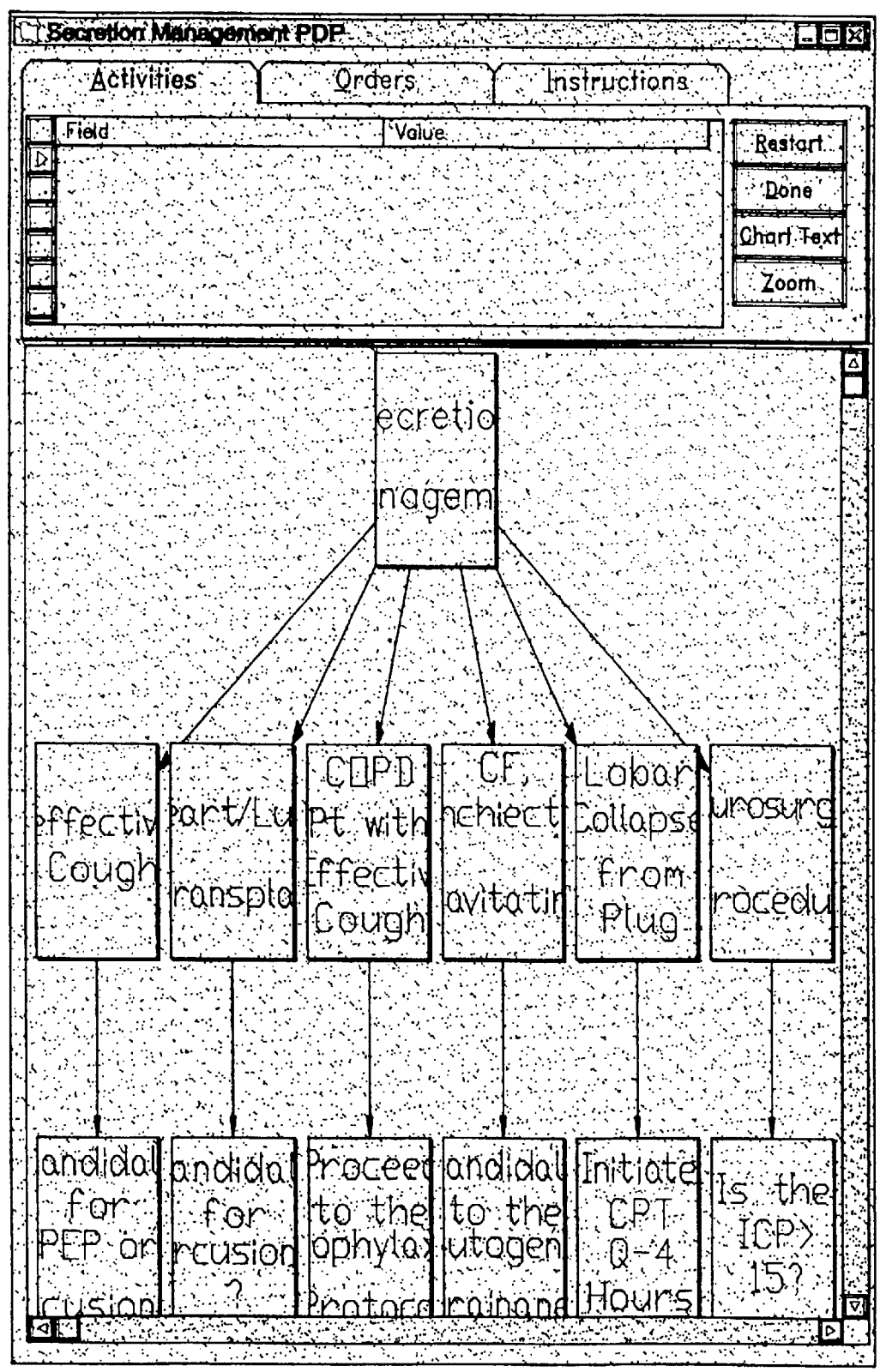
FIG. 3 is a computer screen shot of an enlargement of the graphic flowchart representation of FIG. 2.
Figure 4:
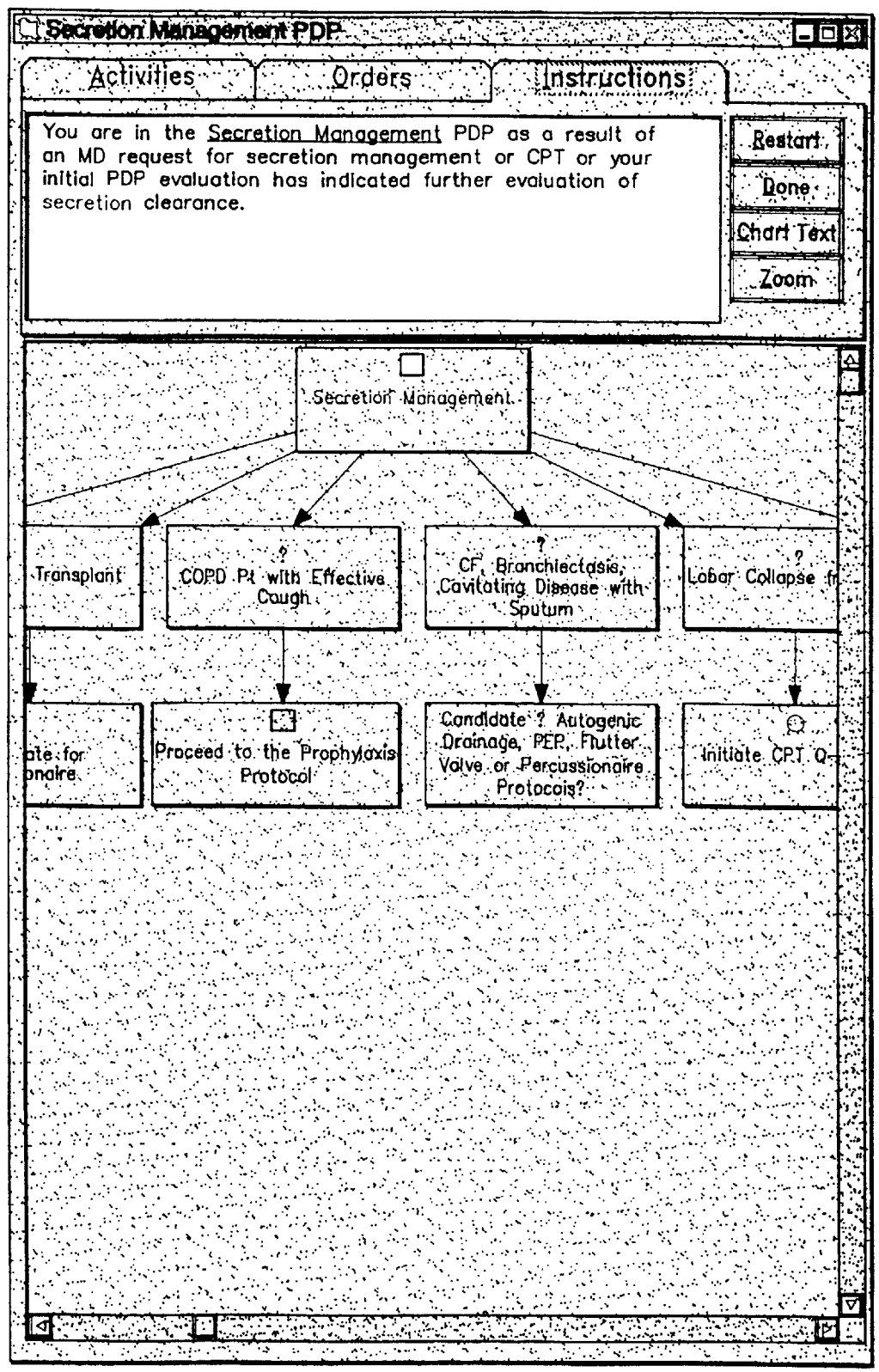
FIG. 4 is computer screen shot of the graphic flowchart representation of FIG. 2 with the Instructions menu selected, showing the initial instructions for the Secretion Management Patient Driven Protocol.
Figure 5:
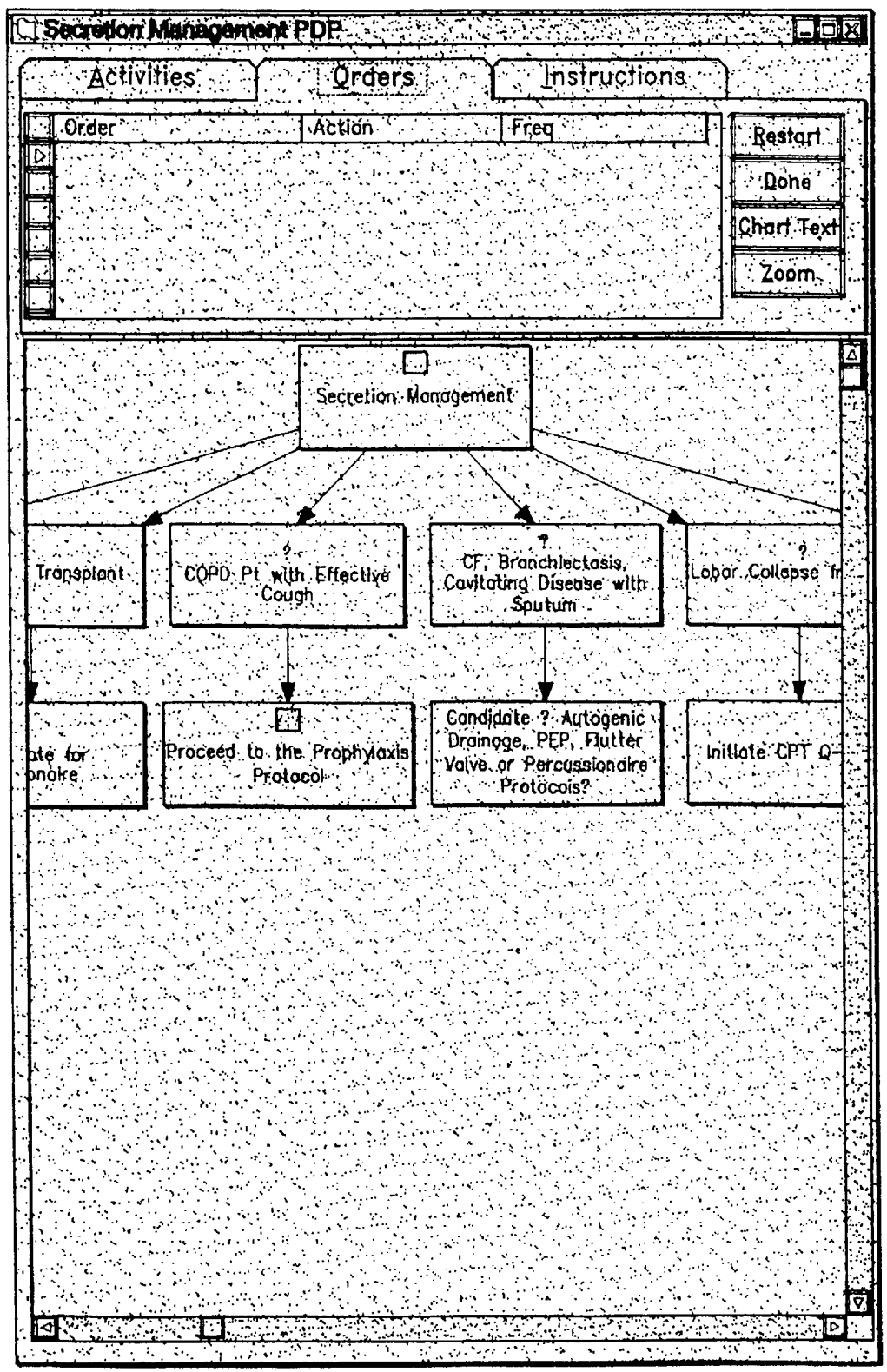
FIG. 5 is a computer screen shot of a graphic flowchart representation of the medical logical module of FIG. 1 with the Orders menu selected.
Figure 6:
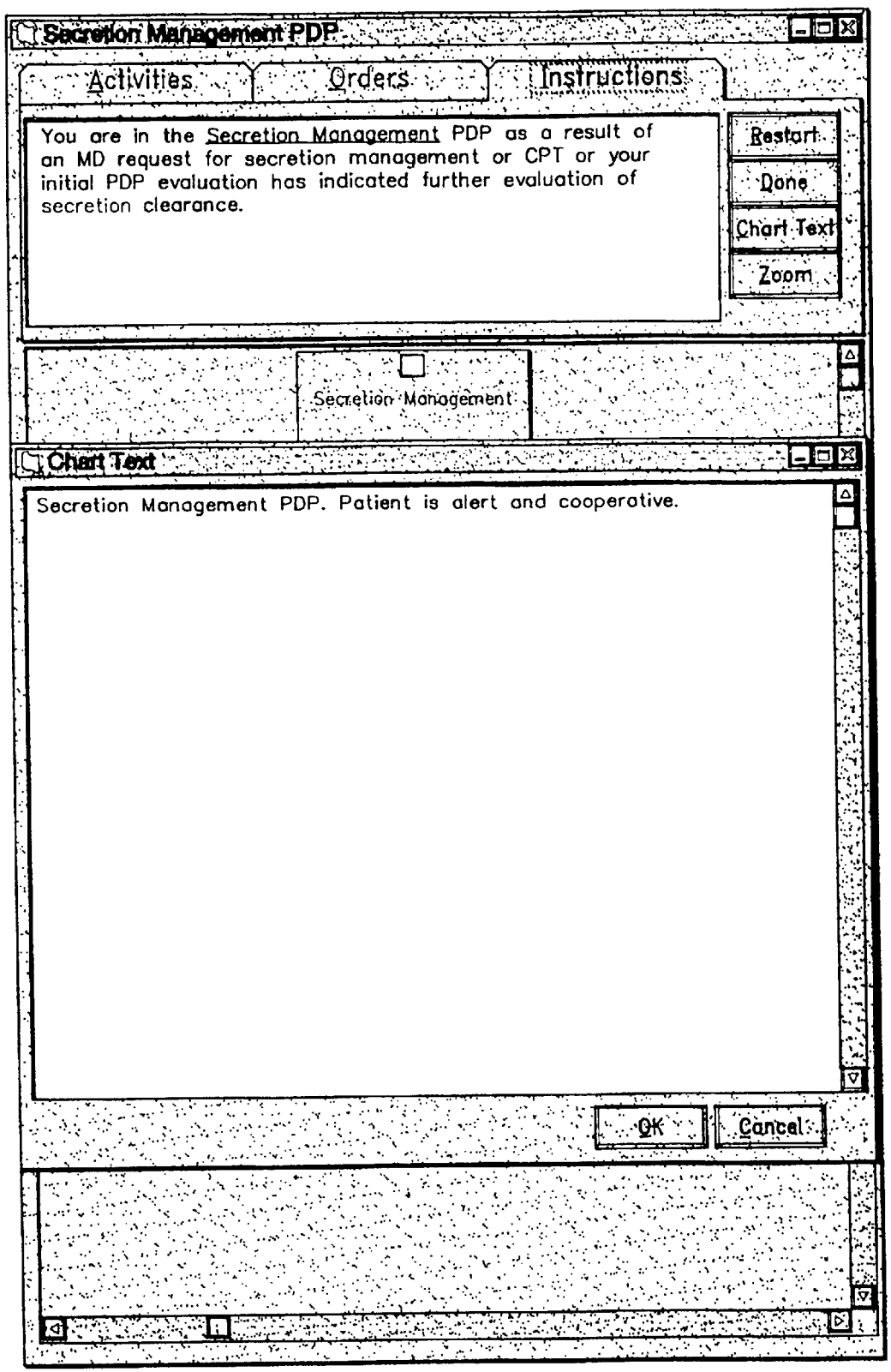
FIG. 6 is a computer screen shot similar to that of FIG. 4, with the Chart Text option selected, and a line of chart text entered.

As is illustrated in the drawings, and with reference to the attached Appendix containing source code for software utilized in the invention, the invention is embodied in an improved system and method for creation of a medical logical module in the Arden syntax file format in an intuitive graphic manner on a computer. The medical logical module designer is able to build the representation of a medical decision process in a form of a flowchart or outline of nodes in the medical decision process. For each node of the flowchart or outline of the decision process, the medical logical module designer is able to define a conditional statement for each path out of the node. The medical logical module designer is then able to define the paths from that node and the conditional statements for the corresponding next node or nodes in the chain, and so on to the concluding node or nodes in the chain. There is no real limit to the number of chaining nodes which can be defined. The concluding node of each branch of the flowchart or outline is an outcome such as a recommended alert, action or order to be taken with the patient as defined by the medical logical module designer.

Once the medical logical module designer has completed the flowchart or outline of the medical decision to be made, the software will automatically generate a medical logical module in the Arden Syntax file format conforming to the then current ASTM standard E31.15 (Health Knowledge Representation). The medical logical module designer would also be able to edit a medical logical module through the use of this graphic editor. The graphic editor software can also read an Arden syntax medical logical module and create a graphic representation of it, for editing or modification, as desired.

The Arden syntax editor hardware and software system of the invention permits graphic creation of Patient Driven Protocols (PDPs), and point of care execution of PDPs. The system provides a software module deliverable on multiple product platforms, including ChartWrite and Vista. The system provides for protocol based care proven to reduce utilization of services.

The Arden syntax editor hardware and software system of the invention provides for the creation and organization of a plurality of protocol nodes, each of which may include information such as a title, and interactive questions for inputting data, yes or no branching to other nodes, an outcome or order, and entering chart text. The key elements of a node typically include instructions for assistance in using the protocol or the particular node, and rules for the conditional statement or node question for determining a path from the node. The key output from a node can typically include rule values, orders, chart text, and an Arden syntax file for a medical logical module. Existing Arden syntax files for an medical logical module can also be imported into the editor.

Referring to FIGS. 1–9, illustrating screen shots of a computer using a "WINDOWS" based operating system available from Microsoft, running an Arden syntax editor developed by Nellcor Puritan Bennett under the name "SmartChart Protocol Editor," in one example, the hardware and software system of the invention can be used to provide a graphic representation of a medical logical module, such as the one entitled a Secretion Management Patient Driven Protocol. The SmartChart Protocol Editor software provides for the creation, organization and use of one or more protocol nodes, each of which may include information such as a title, and interactive node questions for inputting data, or providing conditional statements with a logical truth table "yes" or "no" branching to other nodes, an outcome, and entering of medical chart text. The key elements of a node typically include instructions for assisting the user in using the protocol or the node, and rules for determining a path from the node in response to an answer to a conditional statement or data input. The key output from a node can typically include rule values, orders, chart text, and an Arden syntax file for creation of a medical logical module.

Figure 7:
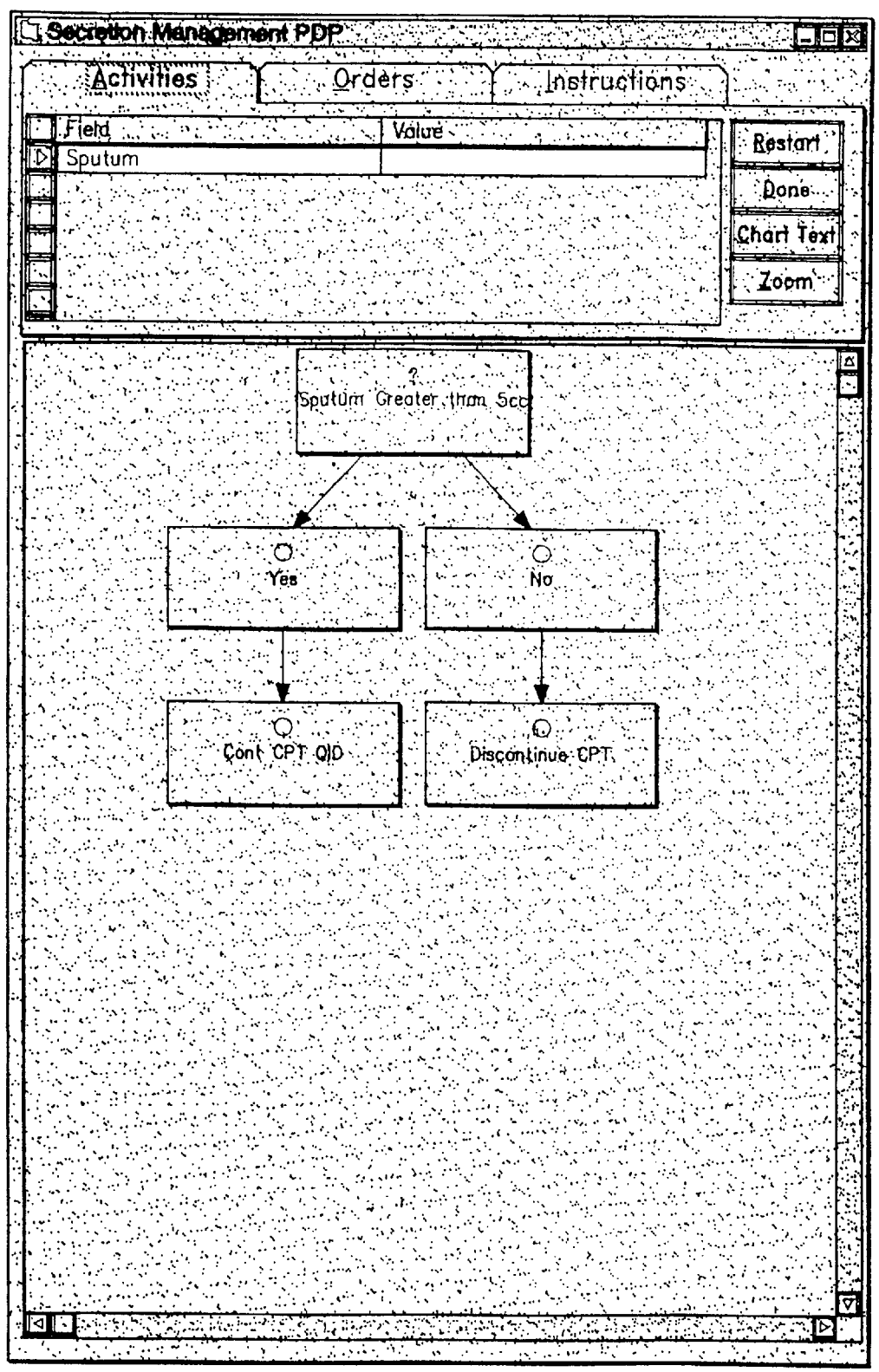
FIG. 7 is a computer screen shot of the graphic flowchart representation of the medical logical module of FIG. 1 with a node question selected showing the paths from the conditional statements of the node question.
Figure 8:
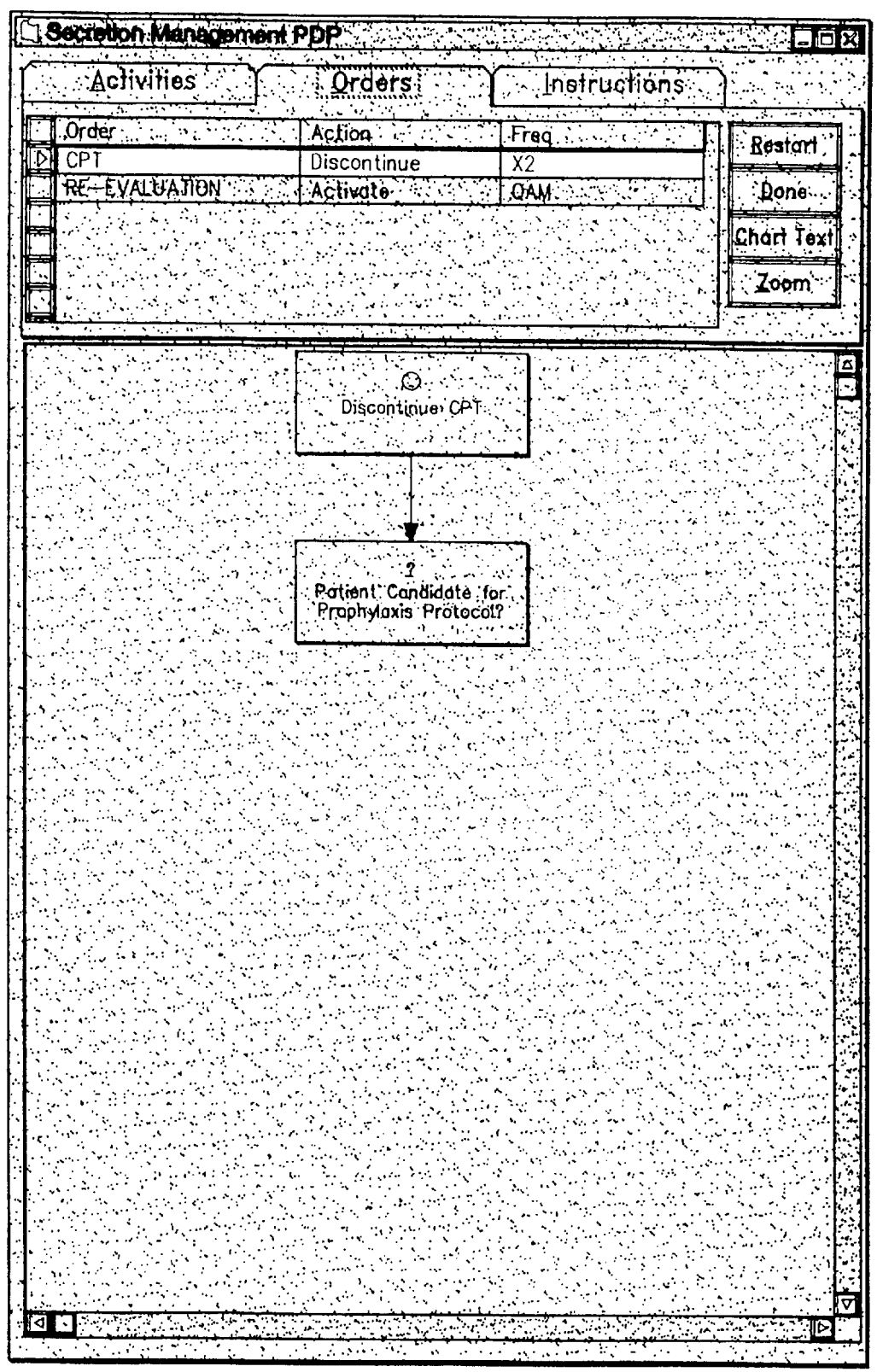
FIG. 8 is a computer screen shot of a branch of the graphic flowchart of FIG. 7 to another node question.
Figure 9:
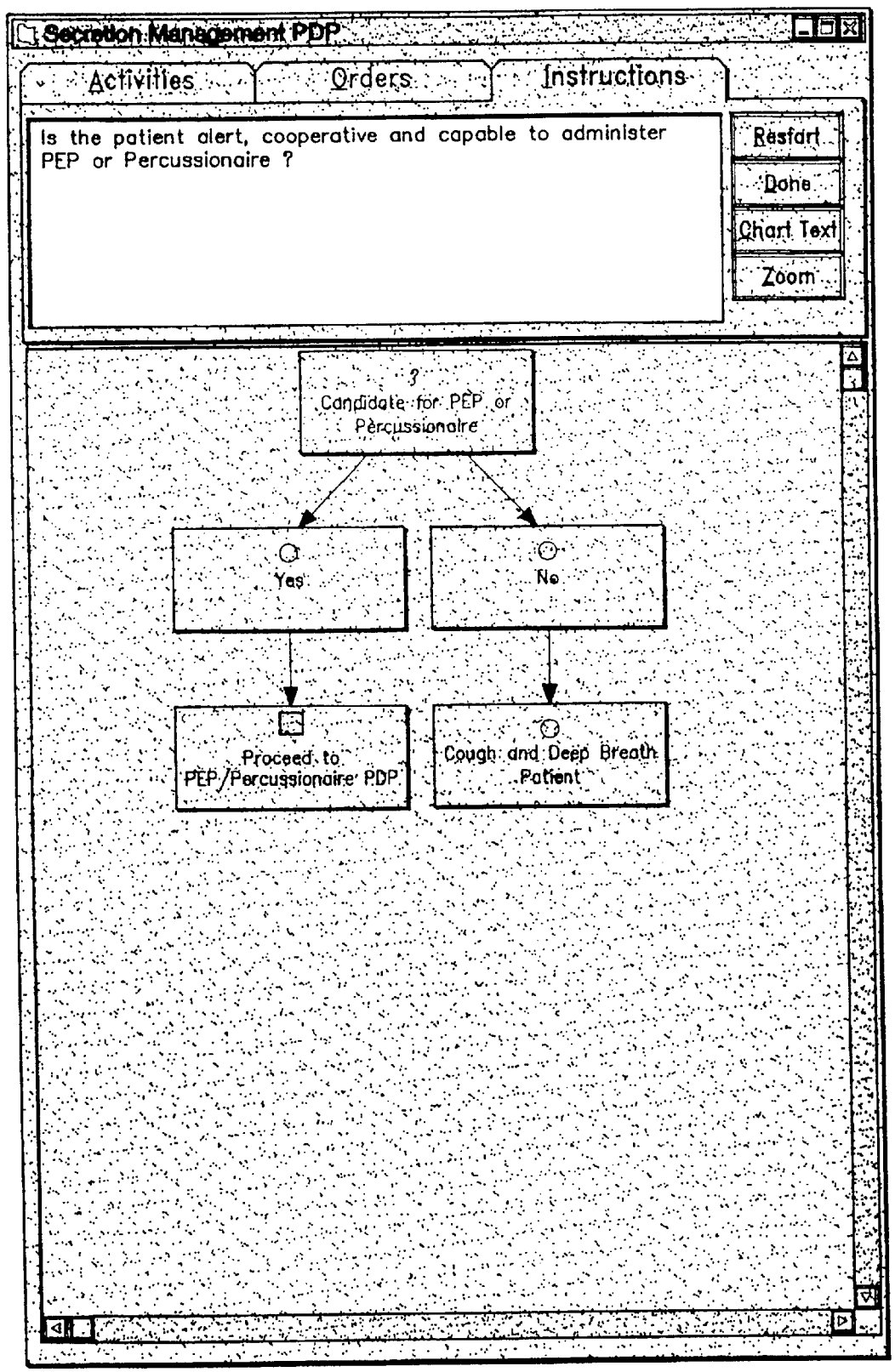
FIG. 9 is a computer screen shot showing the node question of FIG. 8 selected, and showing the paths from the conditional statements of the node question.
Figure 10:
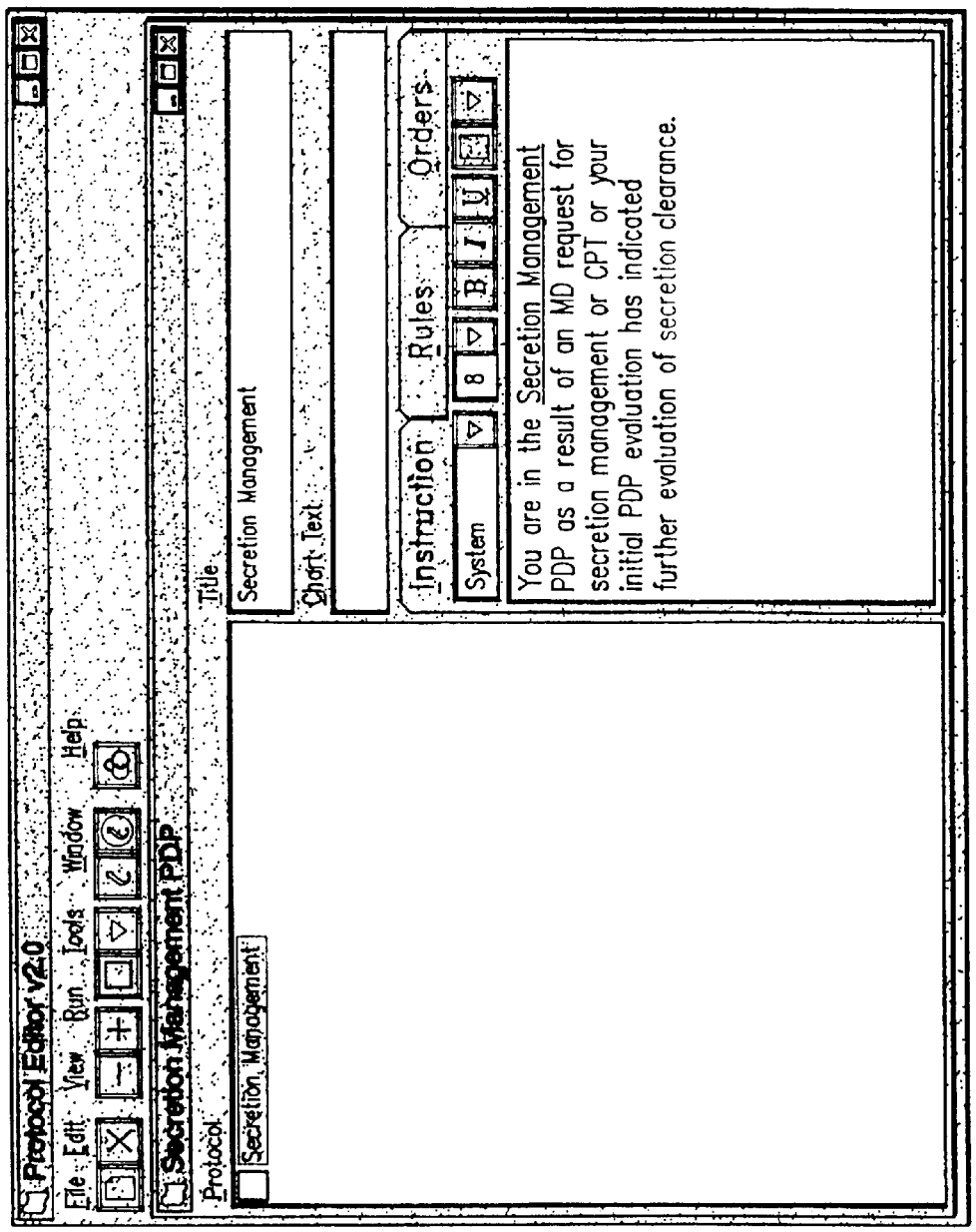
FIG. 10 is a computer screen shot showing an opening screen of a Protocol Editor software with an Instruction window selected for viewing and editing the initial instructions for the Secretion Management Patient Driven Protocol of FIG. 4.
Figure 11:
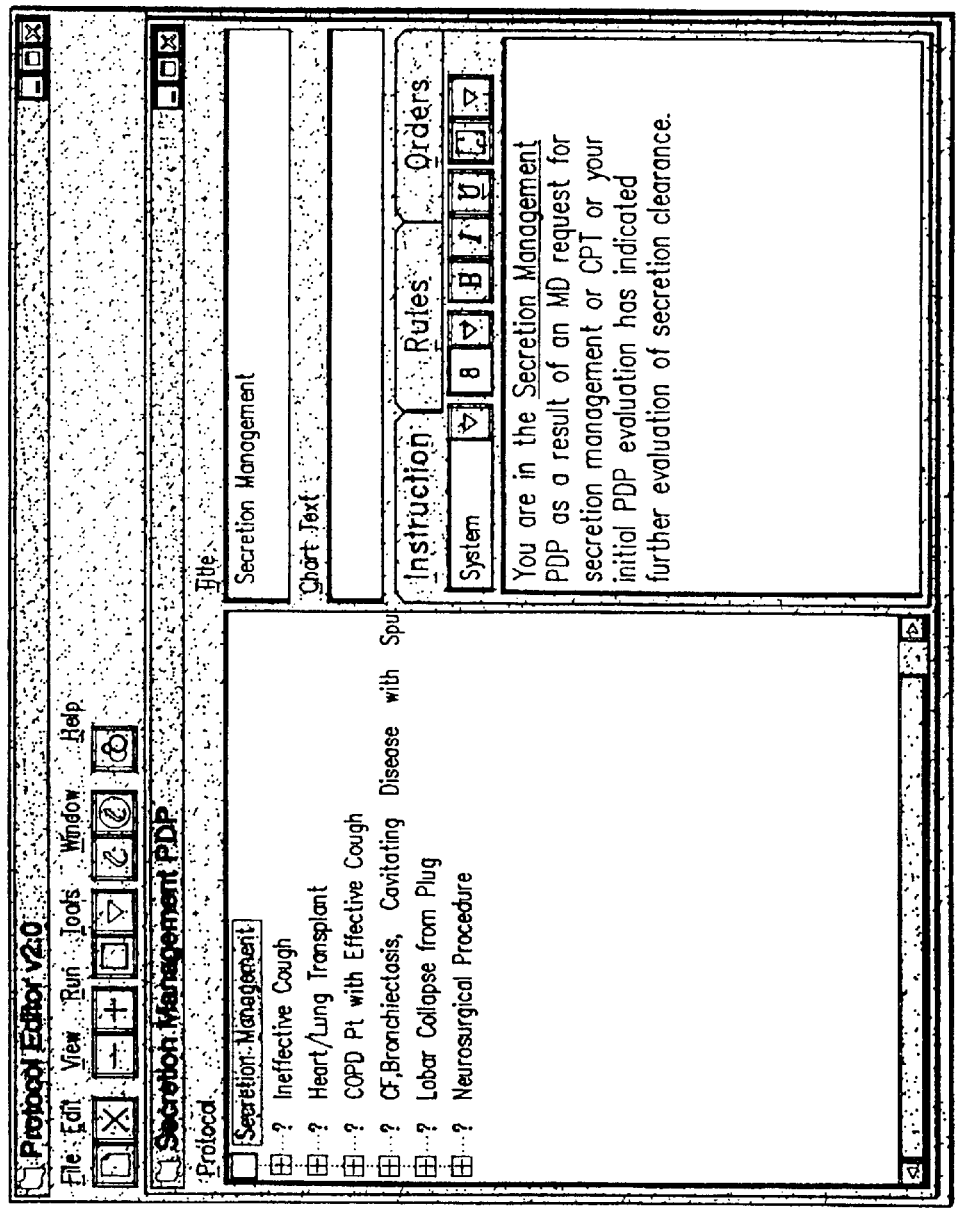
FIG. 11 is a computer screen shot similar to FIG. 10 showing selected intermediate nodes from the protocol as seen in FIG. 2, in outline format.
Figure 12:
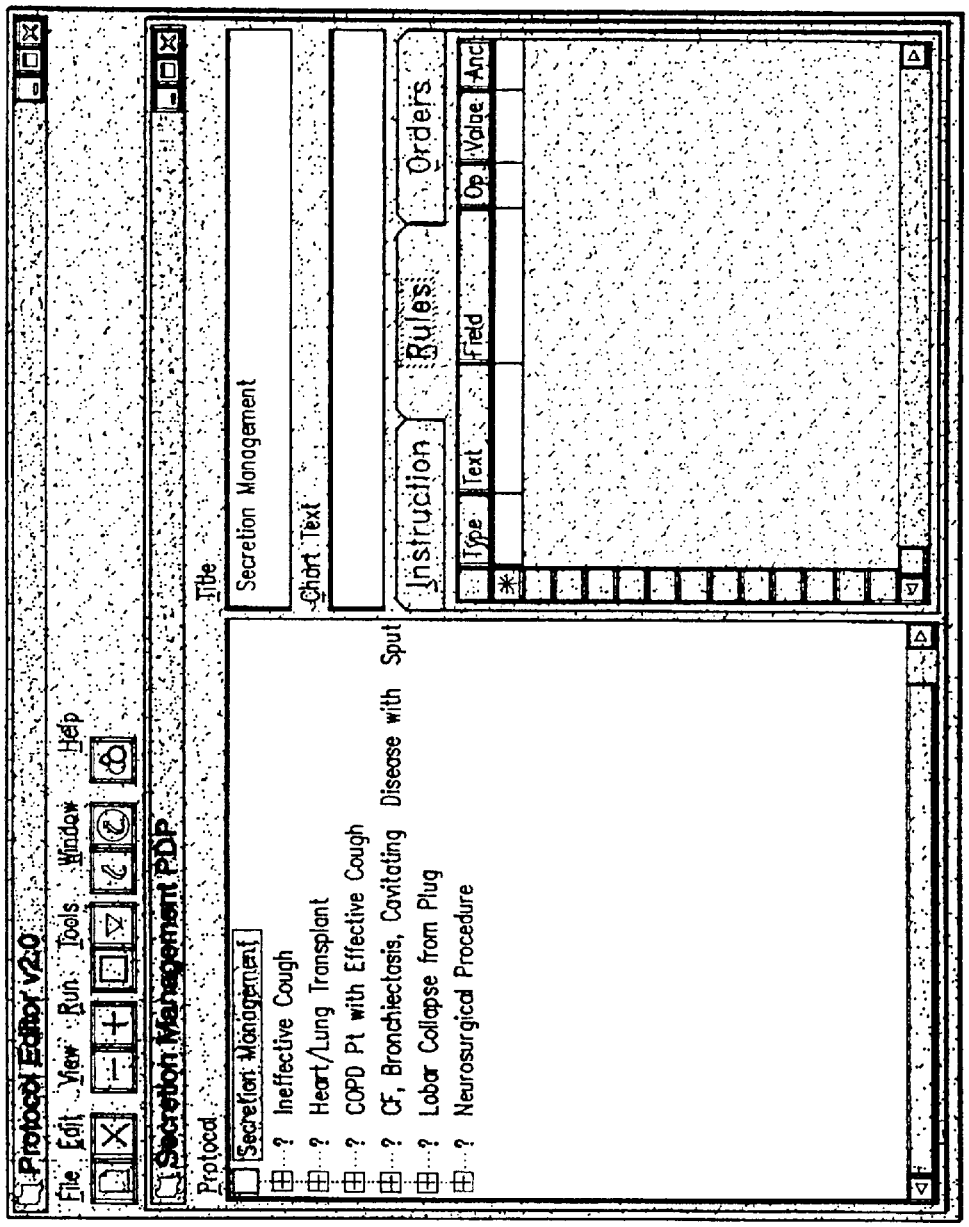
FIG. 12 is a computer screen shot similar to FIG. 10 showing a Rules window selected for viewing and editing the initial rules for the Secretion Management Patient Driven Protocol.
Figure 13:
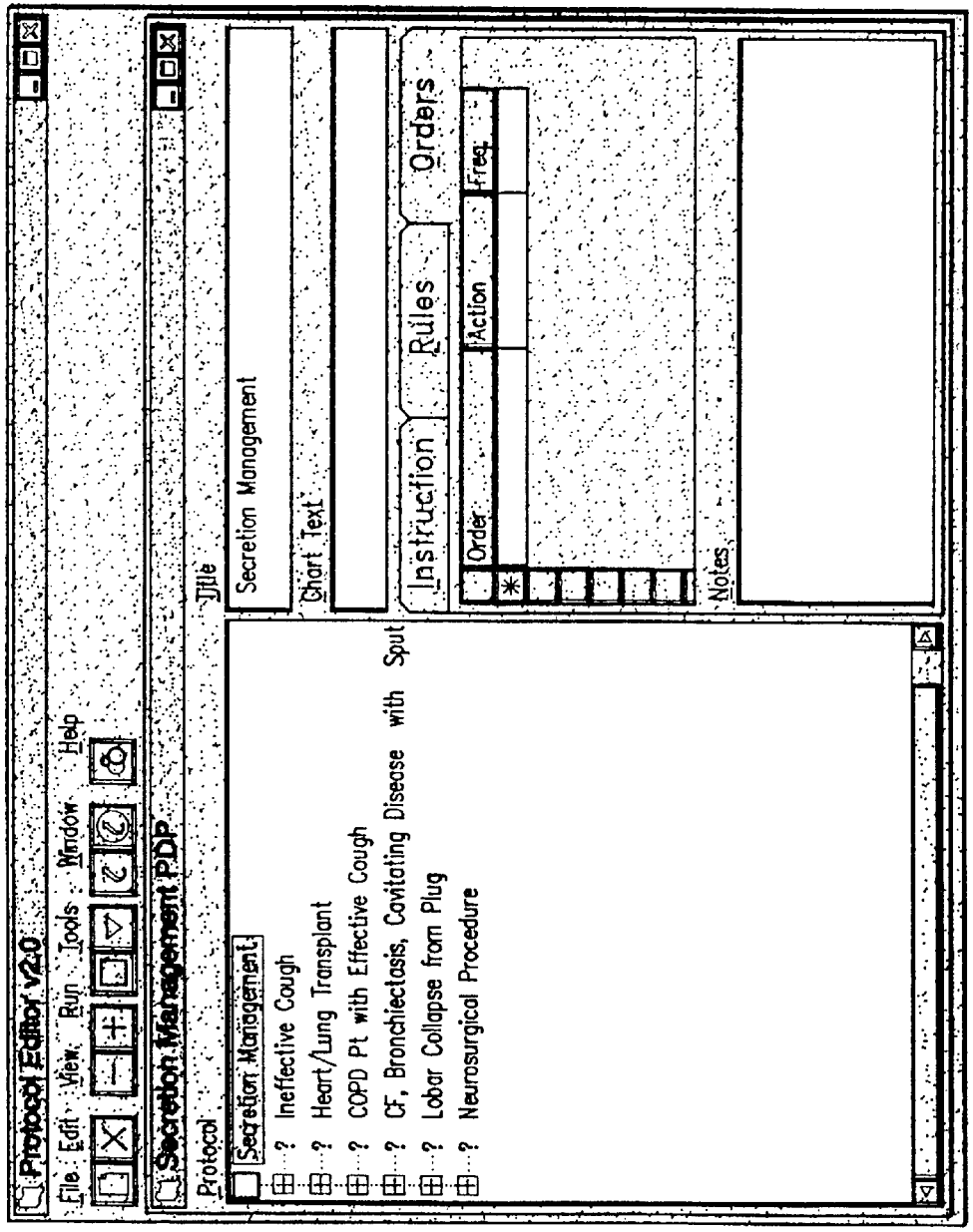
FIG. 13 is a computer screen shot similar to FIG. 10 showing a Orders window selected for viewing and editing the initial orders for the Secretion Management Patient Driven Protocol.
Figure 14:
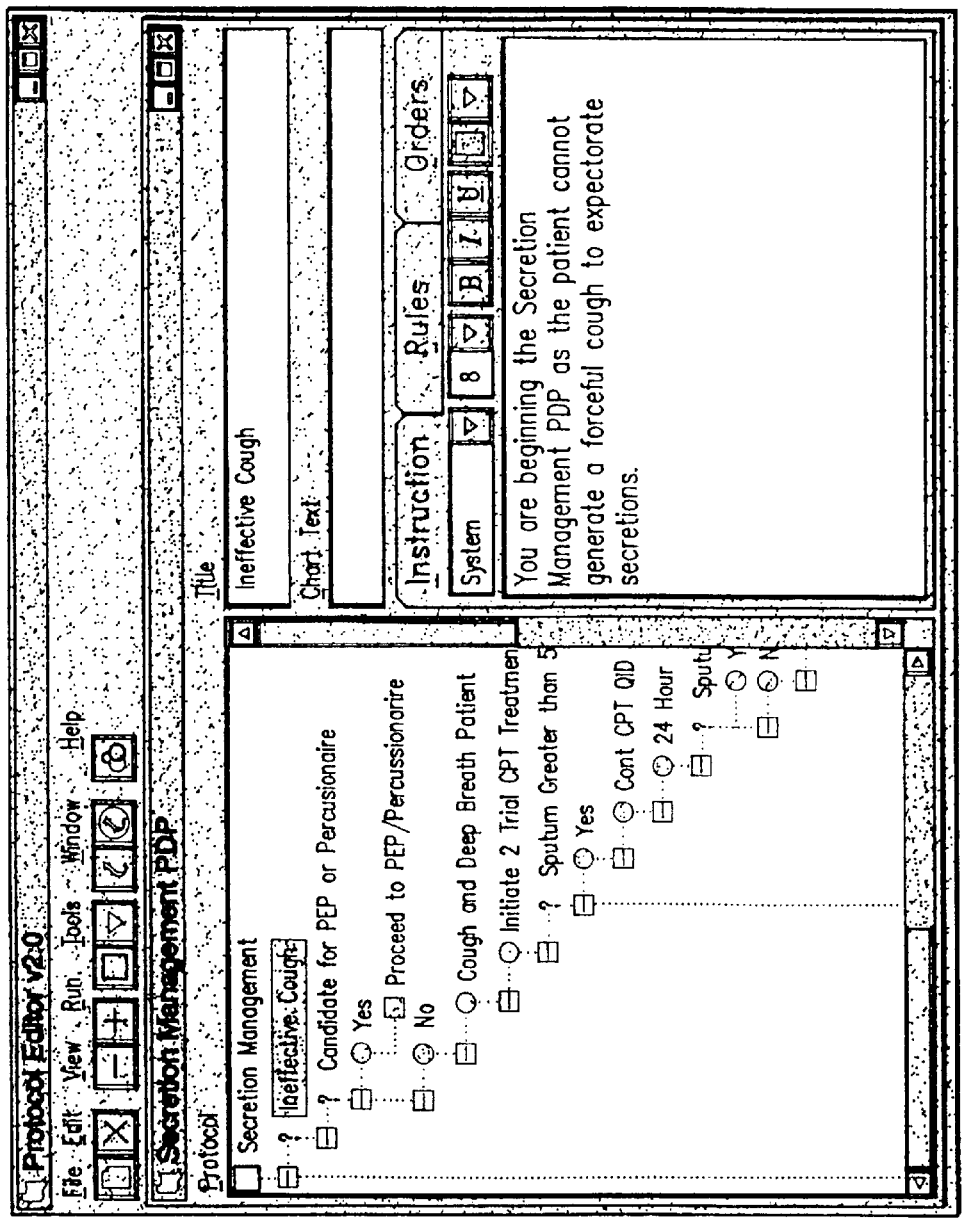
FIG. 14 is a computer screen shot similar to FIG. 10 showing an expanded outline for a selected node question.
Figure 15:
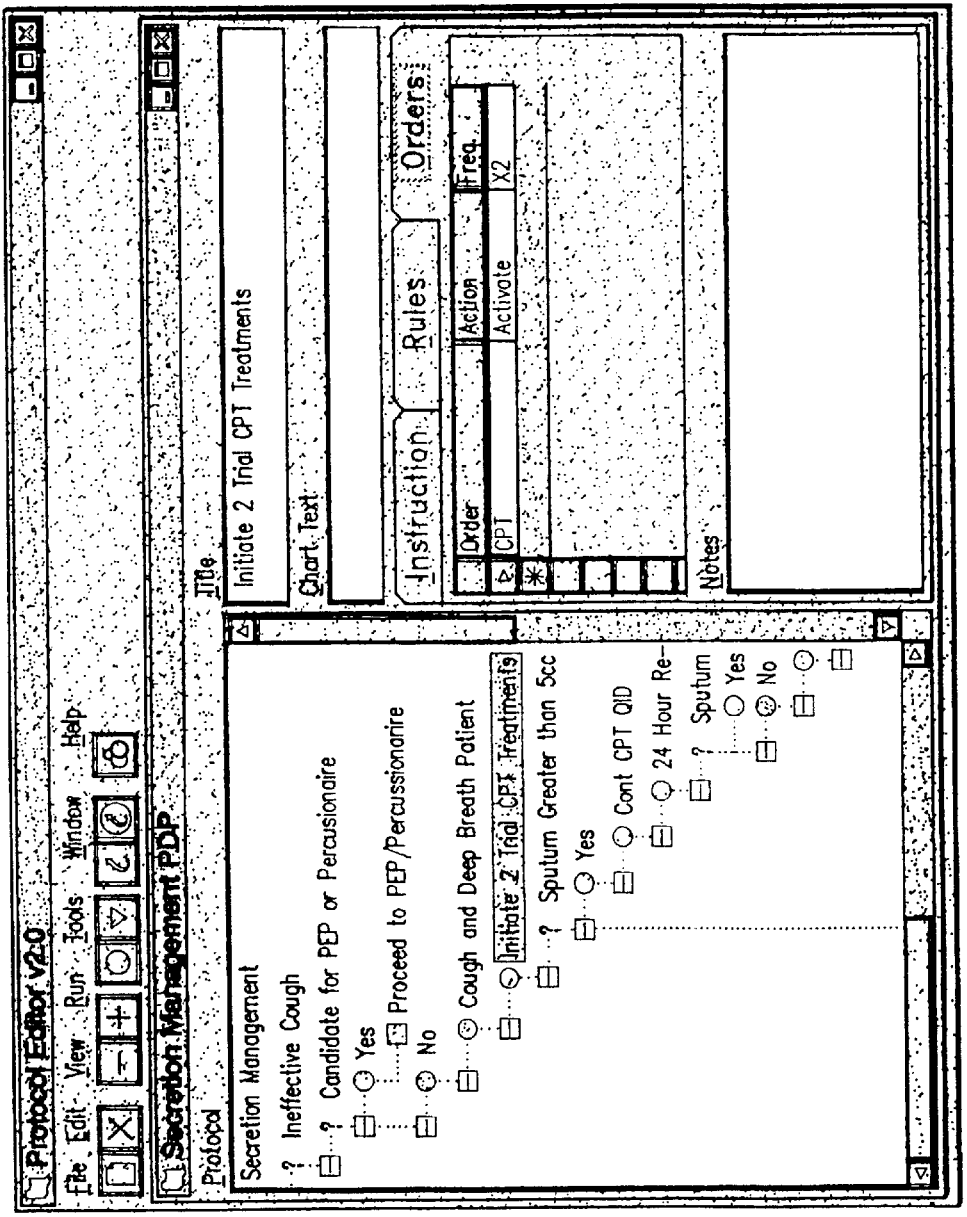
FIG. 15 is a computer screen shot similar to FIG. 14 showing Orders to be generated for the highlighted, selected node.
Figure 16:
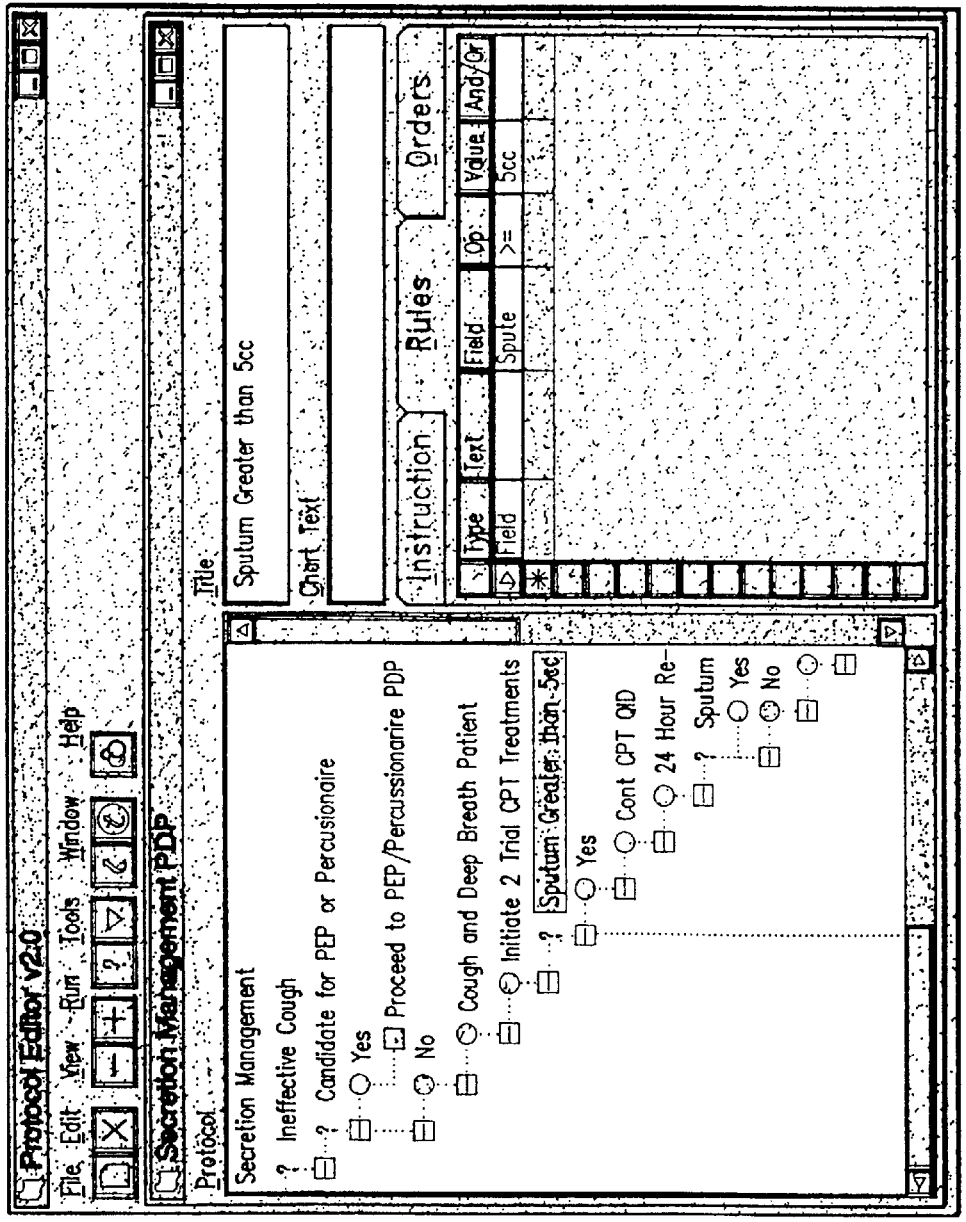
FIG. 16 is a computer screen shot similar to FIG. 15 showing Rules for a conditional statement of the highlighted, selected node.
Figure 17:
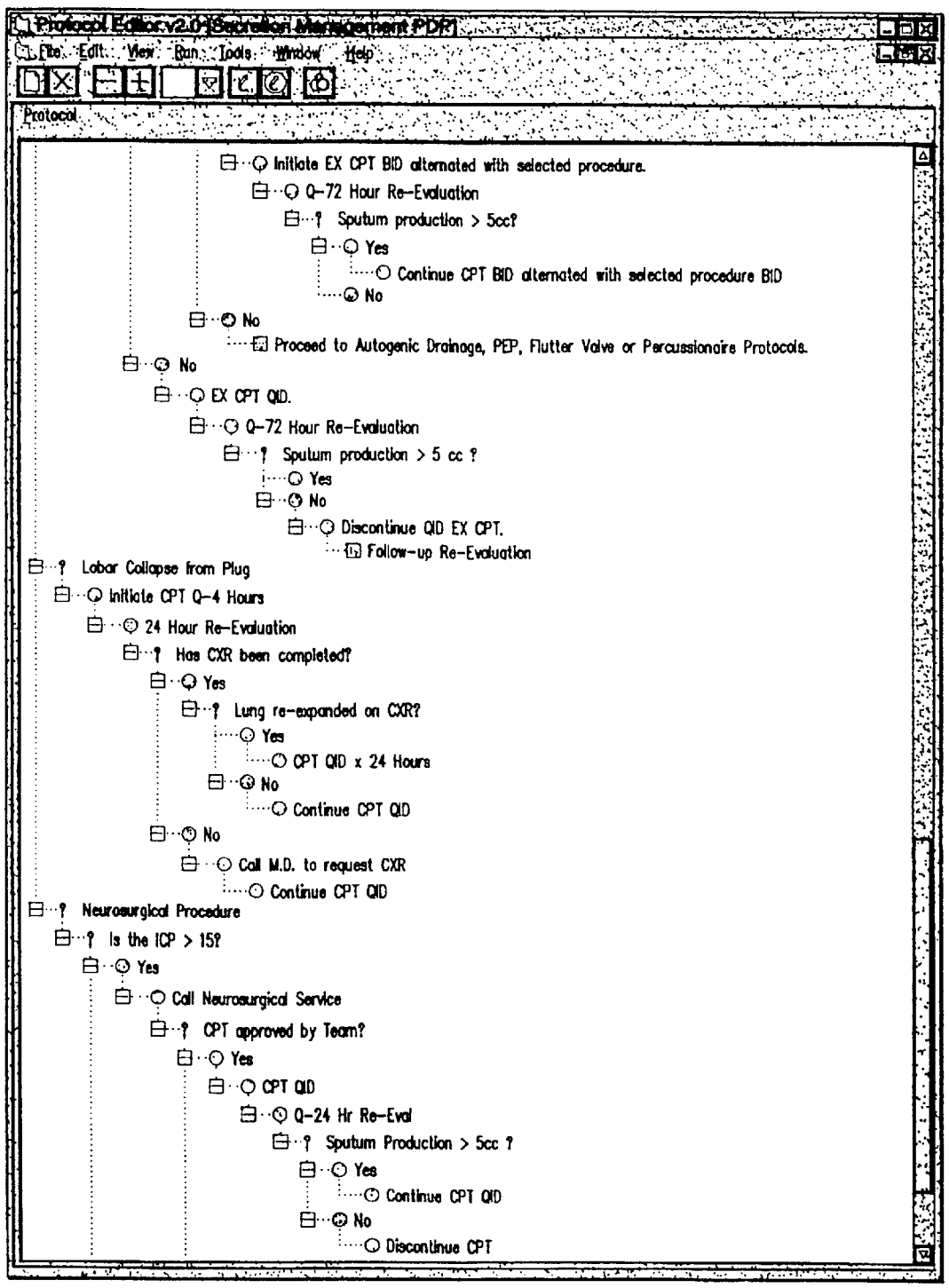
FIG. 17 is a computer screen shot of an expanded window of the node outline shown in FIGS. 14, 15 and 16.
Figure 18:
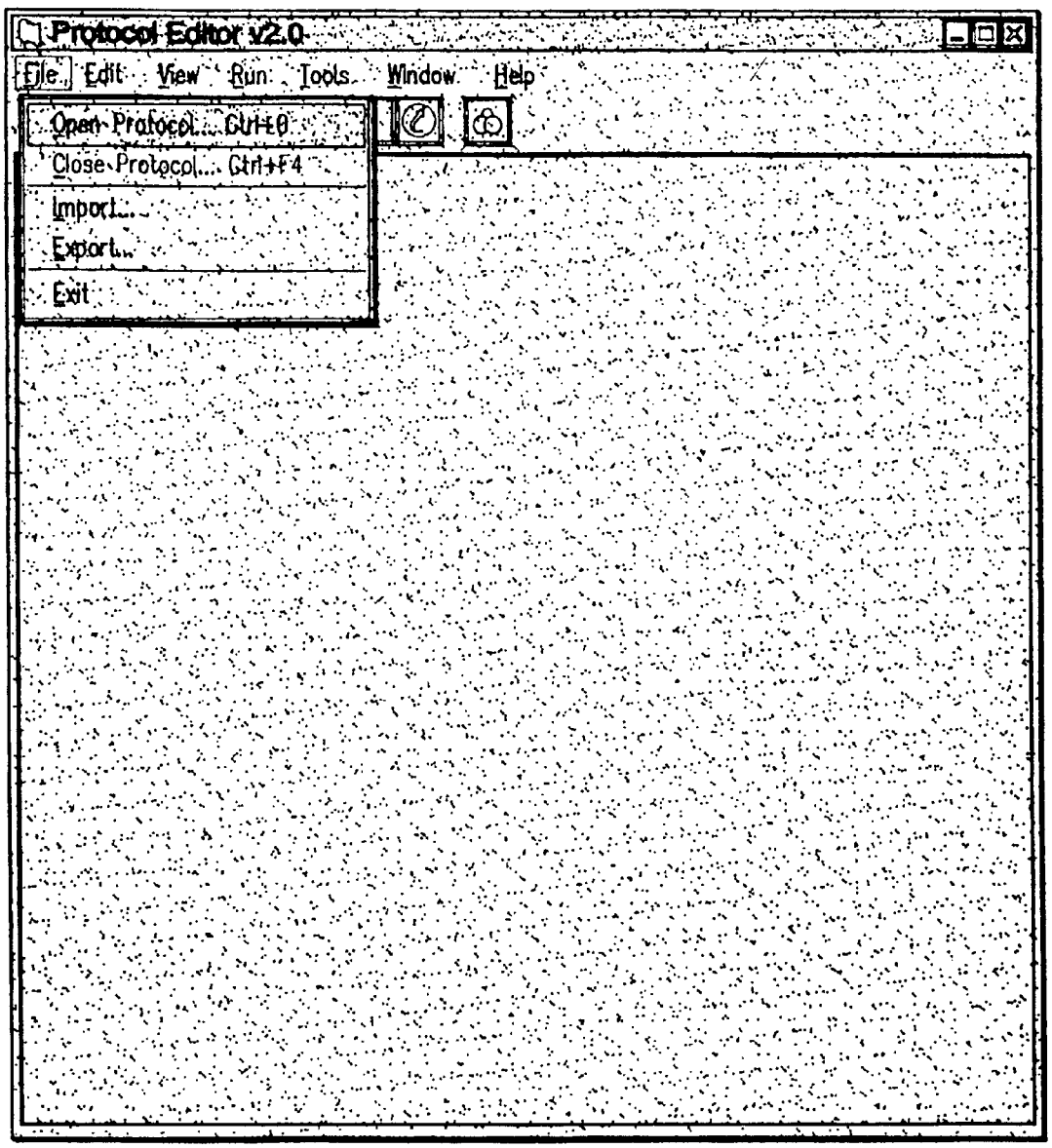
FIG. 18 is a computer screen shot showing the File pull down menu options of the Protocol Editor software of FIG. 10.
Figure 19:
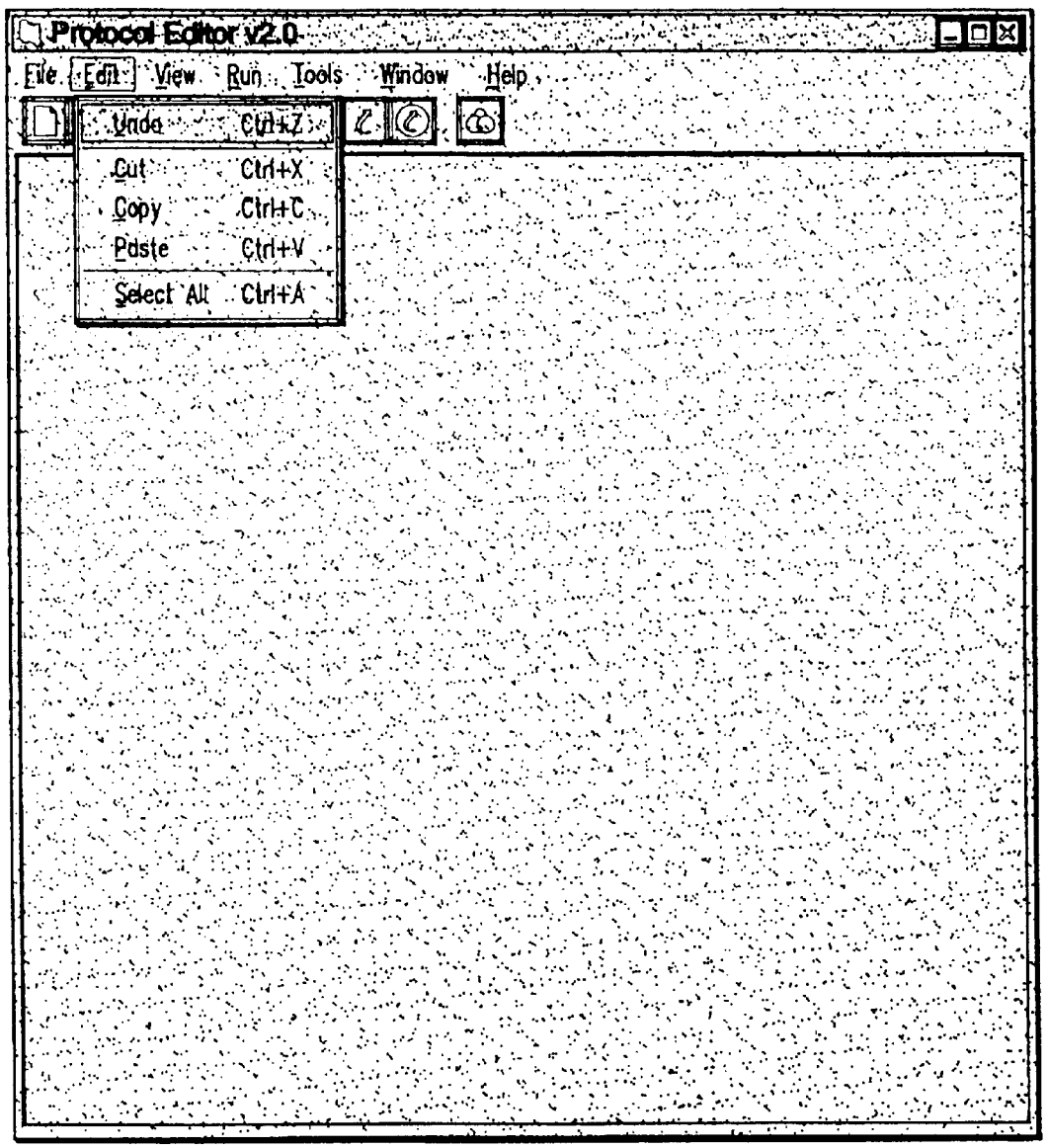
FIG. 19 is a computer screen shot showing the Edit pull down menu options of the Protocol Editor software of FIG. 10.
Figure 20:
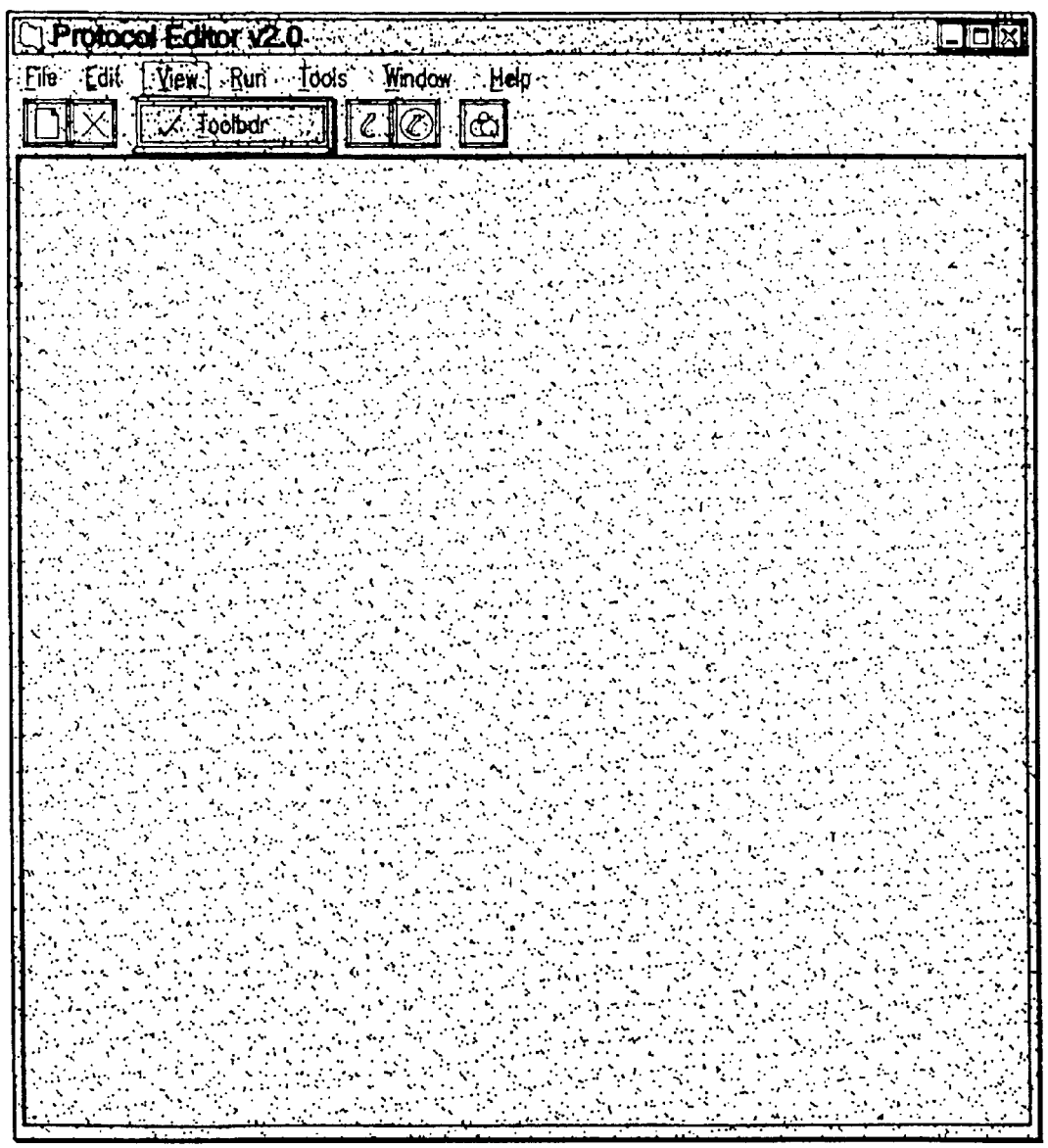
FIG. 20 is a computer screen shot showing the View pull down menu options of the Protocol Editor software of FIG. 10.
Figure 21:
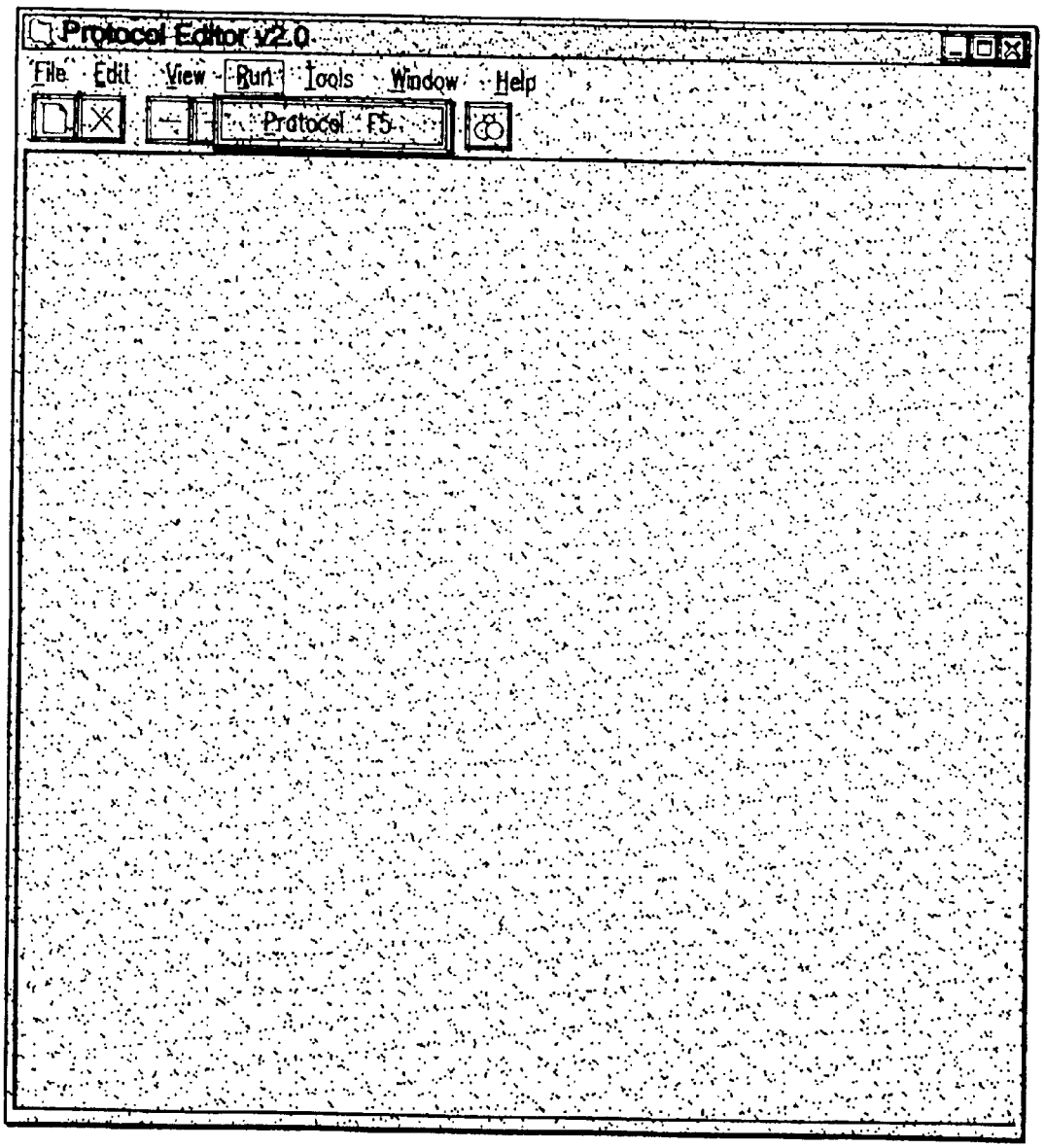
FIG. 21 is a computer screen shot showing the Run menu options of the Protocol Editor software of FIG. 10.
Figure 22:
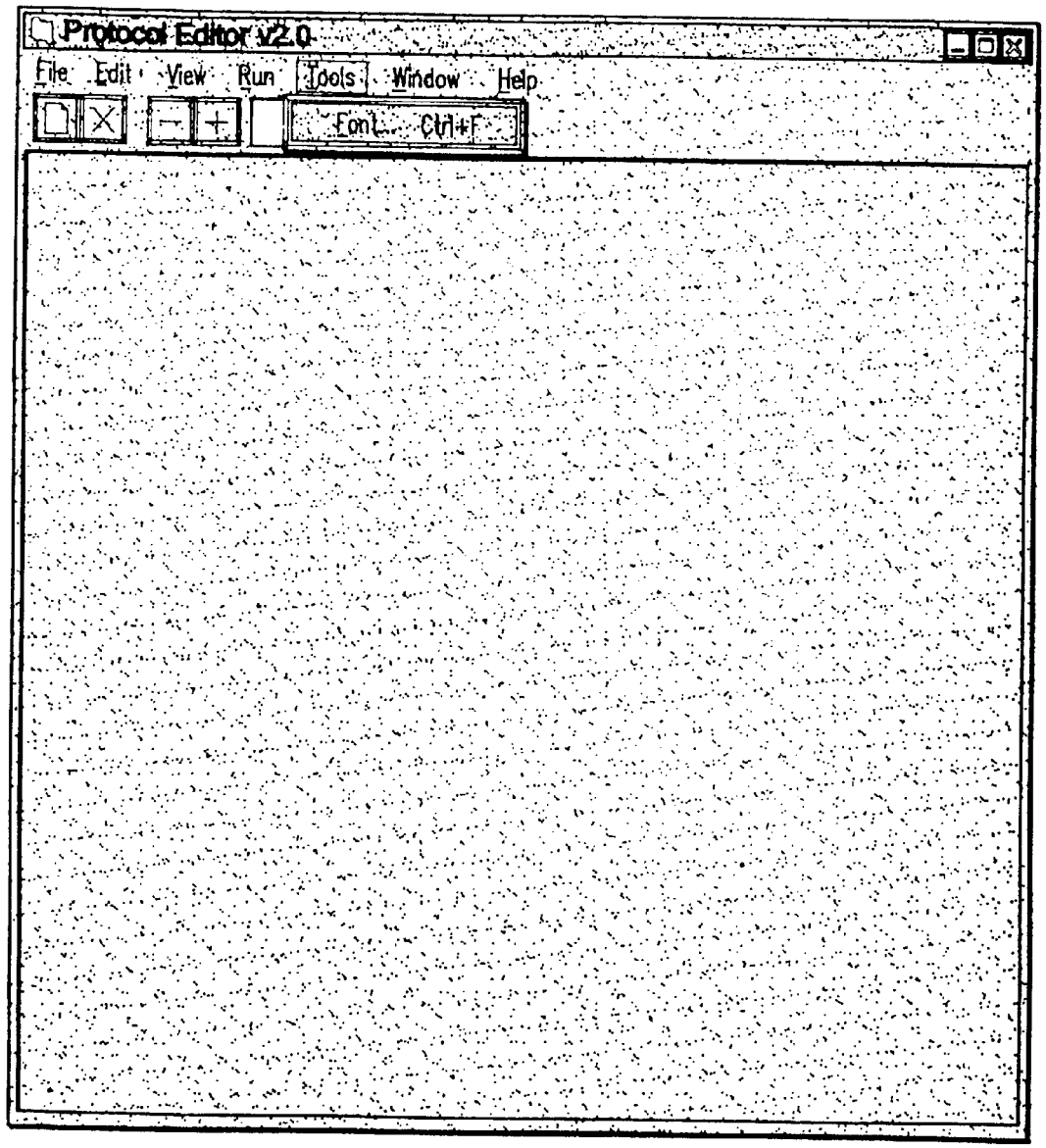
FIG. 22 is a computer screen shot showing the Tools menu options of the Protocol Editor software of FIG. 10.
Figure 23:
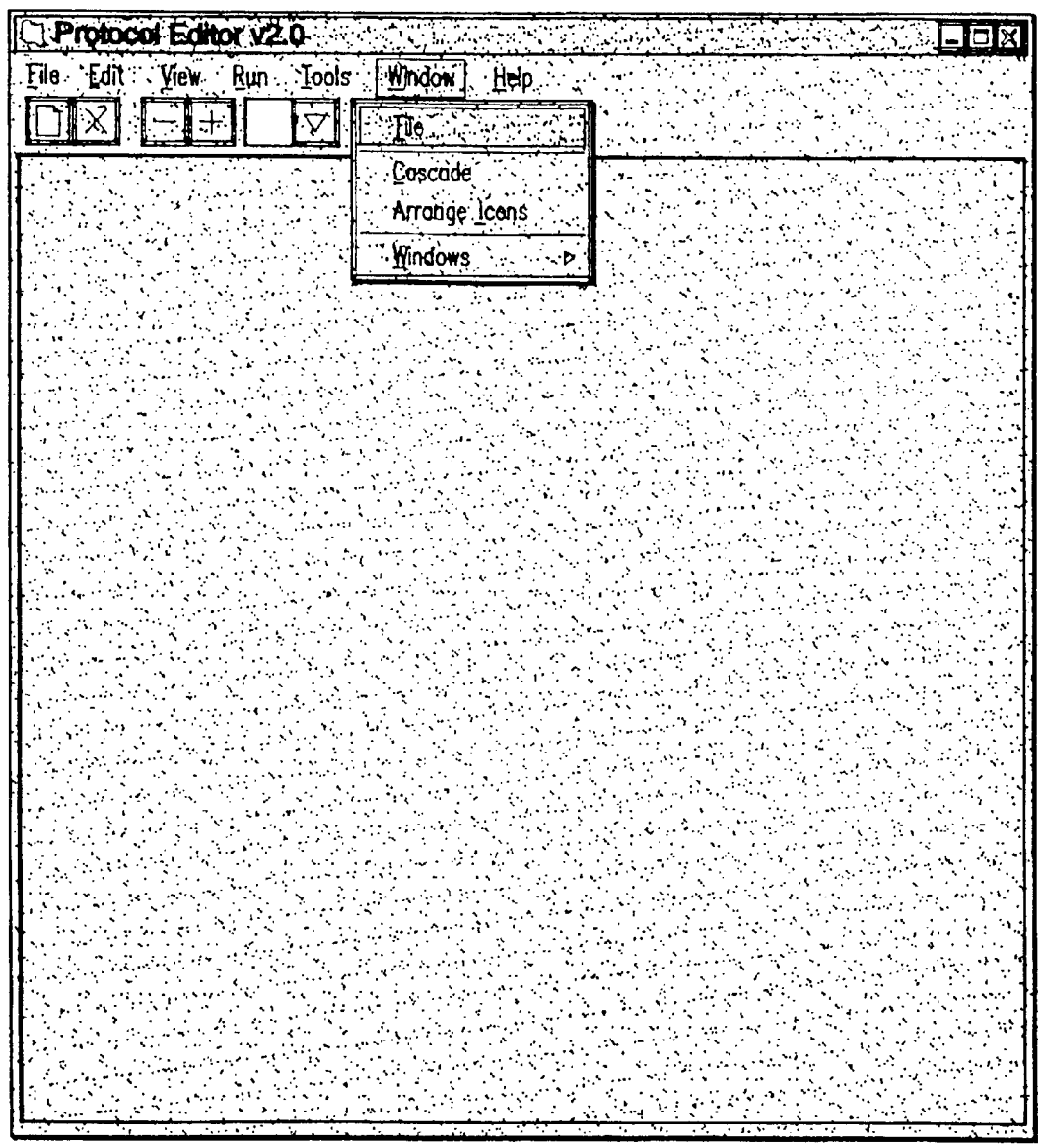
FIG. 23 is a computer screen shot showing the Window menu options of the Protocol Editor software of FIG. 10.
Figure 24:
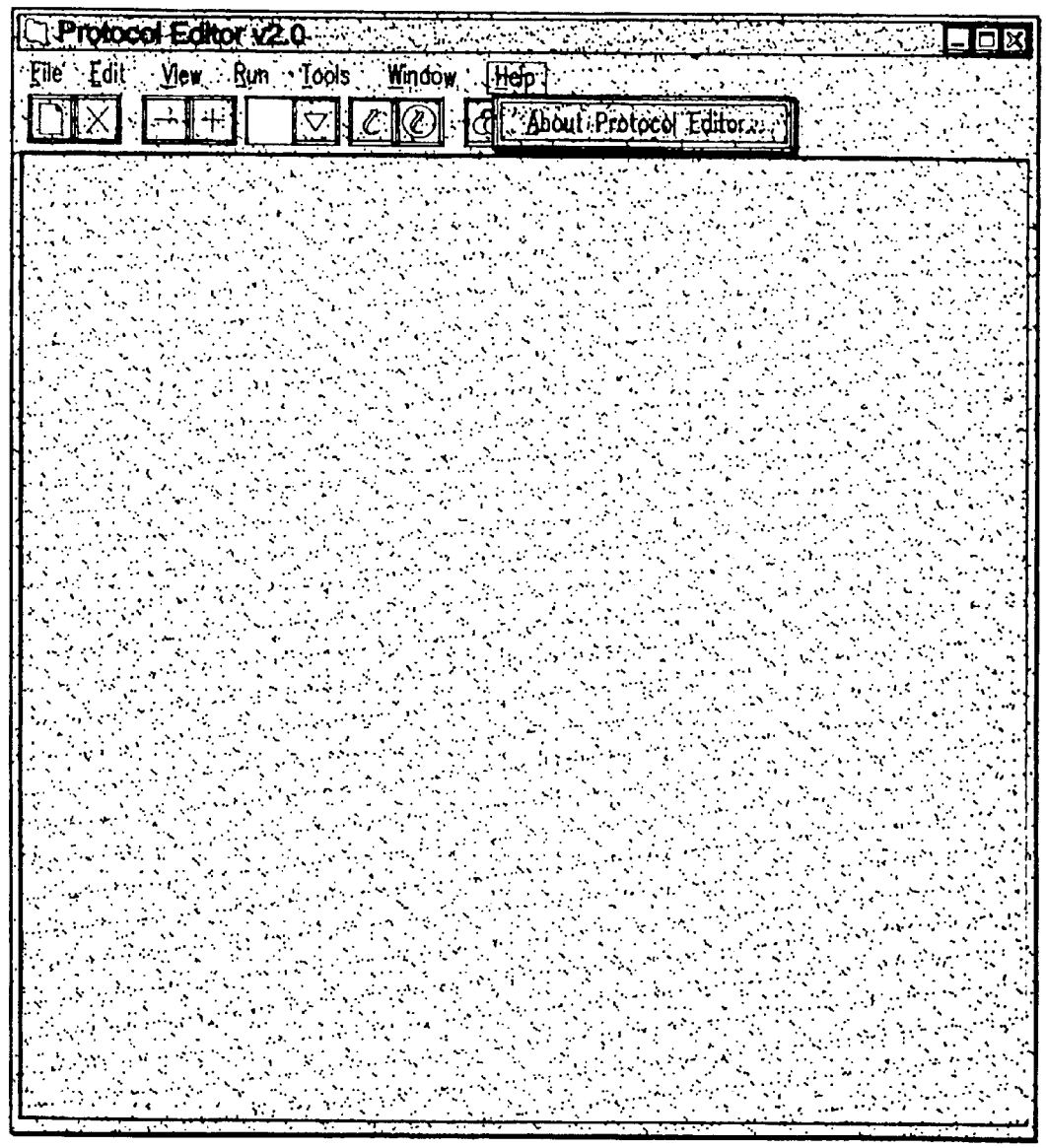
FIG. 24 is a computer screen shot showing the Help menu options of the Protocol Editor software of FIG. 10.
Figure 25:
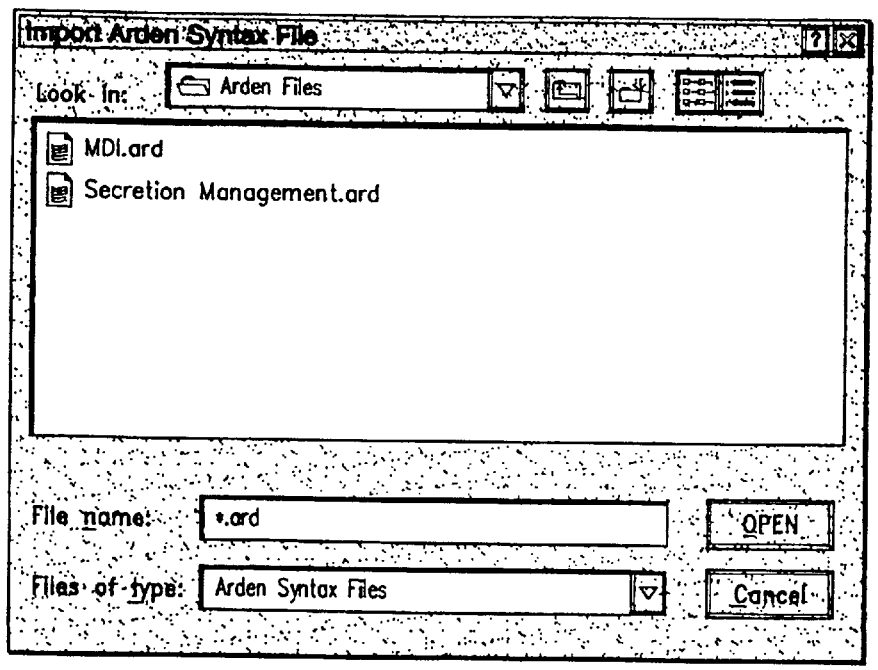
FIG. 25 is a computer screen shot showing the Import option from the Protocol Editor software File options of FIG. 18.
Figure 26:
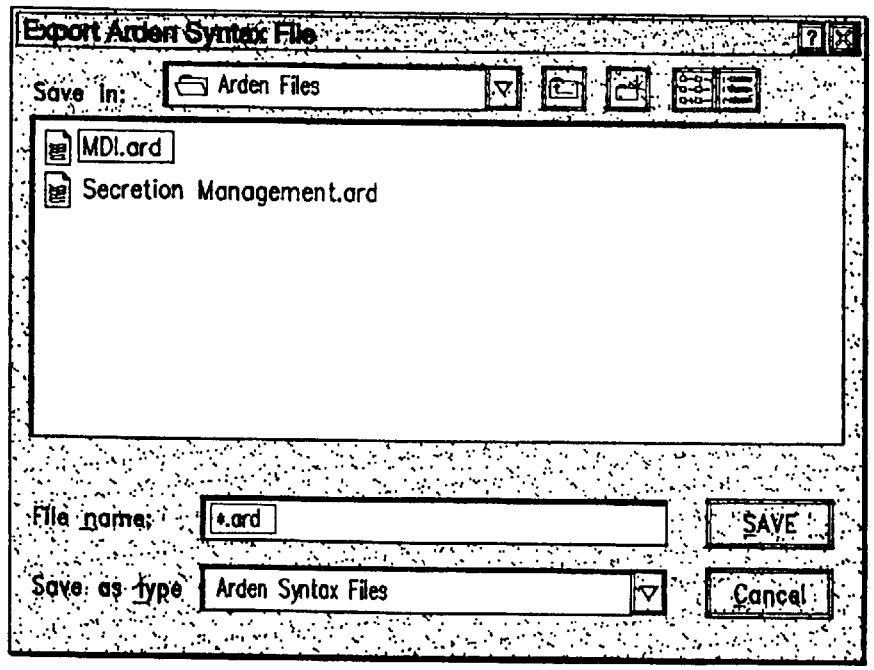
FIG. 26 is a computer screen shot showing the Export option from the Protocol Editor software File options of FIG. 18.

With reference to FIGS. 10–26, the present invention provides for a method and system for creation of a medical logical module, such as in the example, a Secretion Management PDP medical logical module, for a computer in the Arden syntax file format, such as in a WINDOWS based operating system, for example, although other operating systems may of course be suitable. The method of the invention comprises encoding a graphic representation of a medical decision logic tree of a connected series of a plurality of nodes in a medical decision process, each node having a logical path from the node, and each connected series of nodes containing at least one intermediate node and a concluding node. As is illustrated in FIGS. 2–5 and 7–9, the graphic representation preferably can be in the form of a flowchart, and can be presented in the form of an outline, as illustrated in FIGS. 11–17. For each intermediate node, a conditional statement is encoded for each path from the node; a definition of a path from each intermediate node is encoded; and an outcome for each concluding node is encoded, such as is illustrated in FIGS. 7 and 9, and in the outline more fully shown in FIG. 17. In a presently preferred embodiment, the outcome is selected from the group consisting of a recommended alert, an order, an action to be taken with the patient, a coded message, a narrative message, a screen, triggering of another medical logical module, and communicating with another programming application, consistent with outcomes available in Arden syntax, although other outcomes may also be suitable or may become available in the future. A medical logical module of the graphic representation of the protocol being developed or edited, such as the Secretion Management PDP for example, can also be encoded in Arden Syntax file format, which in one presently preferred embodiment conforms to the current ASTM standard E31.15 (Health Knowledge Representation). An existing medical logical module can be imported in the Arden syntax graphic editor of the invention, to create a graphic representation of the existing Arden syntax medical logical module, for editing or use.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A method for creation of a medical logical module for a computer in the Arden syntax file format, the steps of the method comprising:

encoding a graphic representation of a patient driven protocol medical decision logic tree of a connected series of a plurality of nodes in a medical decision process, each said node having a logical path from said node, and each said connected series of nodes containing at least one intermediate node and a concluding node;

encoding a conditional statement for each path from each said intermediate node;

encoding a definition of a path from each said intermediate node;

encoding an outcome for each concluding node; and encoding a medical logical module of said graphic representation in Arden Syntax file format.

2. The method of claim 1, wherein said graphic representation is in a form selected from a flowchart, an outline, and a combination thereof.

3. The method of claim 1, wherein said outcome is selected from the group consisting of a recommended alert, an order, an action to be taken with the patient, a coded message, a narrative message, a screen, triggering of another medical logical module, and communicating with another programming application.

4. A system for creation of a medical logical module for a computer in the Arden syntax file format, comprising:

means for encoding a graphic representation of a patient driven protocol medical decision logic tree of a connected series of a plurality of nodes in a medical decision process, each said node having a logical path from said node, and each said connected series of nodes containing at least one intermediate node and a concluding node;

means for encoding a conditional statement for each path from each said node;

means for encoding a definition of a path from each said intermediate node;

means for encoding an outcome for each concluding node; and means for generating a medical logical module in Arden Syntax file format.

5. The system of claim 4, wherein said is in a form selected from a graphic flowchart, an outline, and a combination thereof.

6. The system of claim 4, wherein said outcome is selected from the group consisting of a recommended alert, action or order to be taken with the patient as defined by the medical logical module designer, a coded message, a narrative message; a screen, which typically results in a message, often sent by e-mail, to a researcher or quality assurance officer informing them of a patient that fits some criteria, triggering another medical logical module, and communicating with another programming application.

* * * * *

UNITED STATES PATENT AND TRADEMARK OFFICE
CERTIFICATE OF CORRECTION

PATENT NO.    : 6,725,447 B1                                      Page 1 of 1
DATED         : April 20, 2004
INVENTOR(S)   : John Gilman, Eric F. Halsey and Michael E. Raymer It is certified that error appears in the above-identified patent and that said Letters Patent is hereby corrected as shown below:

<u>Column 1,</u>
Line 16, delete "Editform" and insert -- Editorfrm --.

Signed and Sealed this

Twenty-eighth Day of September, 2004

JON W. DUDAS
*Director of the United States Patent and Trademark Office*